(12) United States Patent
Devengenzo et al.

(10) Patent No.: US 9,439,732 B2
(45) Date of Patent: Sep. 13, 2016

(54) INSTRUMENT INTERFACE OF A ROBOTIC SURGICAL SYSTEM

(71) Applicant: Intuitive Surgical Operations, Inc., Sunnyvale, CA (US)

(72) Inventors: Roman L. Devengenzo, San Jose, CA (US); Thomas G. Cooper, Menlo Park, CA (US); Joseph P. Orban, III, Norwalk, CT (US); Bruce Michael Schena, Menlo Park, CA (US); Alan E. Loh, Los Altos, CA (US); S. Christopher Anderson, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 123 days.

(21) Appl. No.: 13/960,644

(22) Filed: Aug. 6, 2013

(65) Prior Publication Data
US 2013/0331858 A1  Dec. 12, 2013

Related U.S. Application Data

(63) Continuation of application No. 13/112,452, filed on May 20, 2011, now Pat. No. 8,529,582, which is a continuation of application No. 11/613,695, filed on Dec. 20, 2006, now Pat. No. 7,963,913, which is a
(Continued)

(51) Int. Cl.
*A61B 19/00* (2006.01)

(52) U.S. Cl.
CPC .......... *A61B 19/2203* (2013.01); *Y10S 901/27* (2013.01); *Y10S 901/41* (2013.01)

(58) Field of Classification Search
CPC .............. A61B 19/00; A61B 19/2203; A61B 2019/2234; Y10S 901/41; Y10S 901/27
USPC .......................................... 600/102; 606/130
See application file for complete search history.

(56) References Cited

U.S. PATENT DOCUMENTS

| 1,535,312 A | 4/1925 | Thomas |
| 3,335,719 A | 8/1967 | Boucher |

(Continued)

FOREIGN PATENT DOCUMENTS

| DE | 9304063 U1 | 5/1993 |
| DE | 19537320 A1 | 4/1997 |

(Continued)

OTHER PUBLICATIONS

EP11155101.6 European Search Report, mailed May 26, 2011, 7 pages.
(Continued)

*Primary Examiner* — John P Leubecker

(57) ABSTRACT

An instrument interface of a robotic manipulator and a surgical system including the instrument interface are provided. In one embodiment, the instrument interface includes a spring-loaded input for providing axial load and torque to a sterile adaptor capable of operably coupling an instrument. In another embodiment, a robotic surgical manipulator system includes a manipulator assembly, including a base link operably coupled to a distal end of a manipulator arm, and a carriage link movably coupled to the base link along a lengthwise axis, the carriage link including an integrated instrument interface. The system further includes an instrument operably coupled to the carriage link via the instrument interface, and a processor operably coupled to the manipulator assembly for sensing presence of the instrument.

18 Claims, 26 Drawing Sheets

Related U.S. Application Data continuation-in-part of application No. 11/314,040, filed on Dec. 20, 2005, now Pat. No. 7,666,191, which is a continuation-in-part of application No. 10/922,346, filed on Aug. 19, 2004, now Pat. No. 7,357,774, which is a continuation of application No. 10/004,399, filed on Oct. 30, 2001, now abandoned, which is a continuation of application No. 09/406,360, filed on Sep. 28, 1999, now Pat. No. 6,346,072, which is a continuation of application No. 08/975,617, filed on Nov. 21, 1997, now Pat. No. 6,132,368.

(60) Provisional application No. 60/752,755, filed on Dec. 20, 2005, provisional application No. 60/033,321, filed on Dec. 12, 1996.

(56) References Cited

U.S. PATENT DOCUMENTS

| | | |
|---|---|---|
| 3,494,356 A | 2/1970 | Frederick |
| 3,528,720 A | 9/1970 | Treace |
| 3,622,188 A | 11/1971 | Goeman |
| 3,645,835 A | 2/1972 | Hodgson |
| 3,651,536 A | 3/1972 | Bolzan et al. |
| 3,678,933 A | 7/1972 | Moore et al. |
| 3,698,791 A | 10/1972 | Walchle et al. |
| 3,707,964 A | 1/1973 | Patience et al. |
| 3,724,778 A | 4/1973 | Kuhnlein et al. |
| 3,881,761 A | 5/1975 | Meyer et al. |
| 3,930,380 A * | 1/1976 | Fogt ............... F16D 3/72 185/45 |
| 3,948,552 A | 4/1976 | Hamrick |
| 3,951,495 A | 4/1976 | Donaher et al. |
| 4,038,987 A | 8/1977 | Komiya |
| 4,045,118 A | 8/1977 | Geraci |
| 4,099,614 A | 7/1978 | Heissenberger |
| 4,149,278 A | 4/1979 | Frosch et al. |
| 4,183,613 A | 1/1980 | Walchle et al. |
| 4,240,604 A | 12/1980 | Brach |
| 4,245,985 A * | 1/1981 | Eibofner ............... A61C 1/185 433/105 |
| 4,270,367 A * | 6/1981 | Santore ............... F16D 3/06 403/109.3 |
| 4,281,447 A | 8/1981 | Miller et al. |
| 4,332,066 A | 6/1982 | Hailey et al. |
| 4,367,998 A | 1/1983 | Causer |
| 4,386,933 A | 6/1983 | Sanchez |
| 4,392,485 A | 7/1983 | Hiltebrandt |
| 4,456,960 A | 6/1984 | Wakai |
| 4,457,026 A | 7/1984 | Morris |
| 4,486,928 A | 12/1984 | Tucker et al. |
| 4,494,712 A | 1/1985 | Godwin et al. |
| 4,500,065 A | 2/1985 | Hennekes et al. |
| 4,508,280 A | 4/1985 | Hayosh et al. |
| 4,511,305 A | 4/1985 | Kawai et al. |
| 4,512,709 A | 4/1985 | Hennekes et al. |
| 4,561,540 A | 12/1985 | Hunter et al. |
| 4,573,452 A | 3/1986 | Greenberg |
| 4,602,623 A | 7/1986 | Cherkassky |
| 4,647,643 A | 3/1987 | Zdrahala et al. |
| 4,696,544 A | 9/1987 | Costella |
| 4,705,038 A | 11/1987 | Sjostrom et al. |
| 4,706,372 A | 11/1987 | Ferrero et al. |
| 4,710,093 A | 12/1987 | Zimmer et al. |
| 4,716,811 A | 1/1988 | Johnson |
| 4,744,363 A | 5/1988 | Hasson |
| 4,751,925 A | 6/1988 | Tontarra |
| 4,766,775 A | 8/1988 | Hodge |
| 4,793,053 A | 12/1988 | Zuccaro et al. |
| 4,799,779 A | 1/1989 | Mesmer |
| 4,799,799 A | 1/1989 | Sapko et al. |
| 4,809,747 A | 3/1989 | Choly et al. |
| 4,830,569 A | 5/1989 | Jannborg |
| 4,832,198 A | 5/1989 | Alikhan |
| 4,834,090 A | 5/1989 | Moore |
| 4,837,703 A | 6/1989 | Kakazu et al. |
| 4,848,758 A | 7/1989 | Mills |
| 4,863,204 A | 9/1989 | Peters |
| 4,905,710 A | 3/1990 | Jones |
| 4,915,563 A | 4/1990 | Teillauchet et al. |
| 4,919,112 A | 4/1990 | Siegmund |
| 4,928,546 A | 5/1990 | Walters |
| 4,943,939 A | 7/1990 | Hoover |
| 4,979,949 A | 12/1990 | Matsen, III |
| 4,980,963 A | 1/1991 | Dinse |
| 4,996,975 A | 3/1991 | Nakamura |
| 5,018,266 A | 5/1991 | Hutchinson et al. |
| 5,051,000 A * | 9/1991 | Cadwallader ............ F16C 29/00 384/10 |
| 5,052,396 A | 10/1991 | Wedel et al. |
| 5,052,402 A | 10/1991 | Bencini et al. |
| 5,055,660 A | 10/1991 | Bertagna et al. |
| 5,077,506 A | 12/1991 | Krause |
| 5,078,140 A | 1/1992 | Kwoh |
| 5,080,108 A | 1/1992 | Roth |
| 5,086,401 A | 2/1992 | Glassman et al. |
| 5,122,904 A | 6/1992 | Fujiwara et al. |
| 5,133,735 A | 7/1992 | Slater et al. |
| 5,143,453 A | 9/1992 | Weynant |
| 5,154,717 A | 10/1992 | Matsen, III et al. |
| 5,155,693 A | 10/1992 | Altmayer et al. |
| 5,174,300 A | 12/1992 | Bales et al. |
| 5,176,702 A | 1/1993 | Bales et al. |
| 5,184,601 A | 2/1993 | Putman |
| 5,207,213 A | 5/1993 | Auhll et al. |
| 5,217,003 A | 6/1993 | Wilk |
| 5,221,283 A | 6/1993 | Chang |
| 5,236,432 A | 8/1993 | Matsen, III et al. |
| 5,243,266 A | 9/1993 | Kasagami et al. |
| 5,251,127 A | 10/1993 | Raab |
| 5,255,429 A | 10/1993 | Nishi et al. |
| 5,257,998 A | 11/1993 | Ota et al. |
| 5,259,690 A | 11/1993 | Legge |
| 5,271,384 A | 12/1993 | McEwen et al. |
| 5,274,500 A | 12/1993 | Dunn |
| 5,275,608 A | 1/1994 | Forman et al. |
| 5,284,487 A | 2/1994 | Hartmeister |
| 5,294,209 A | 3/1994 | Naka et al. |
| 5,295,933 A | 3/1994 | Ciminski et al. |
| 5,305,203 A | 4/1994 | Raab |
| 5,312,212 A | 5/1994 | Naumec |
| 5,313,935 A | 5/1994 | Kortenbach et al. |
| 5,316,541 A | 5/1994 | Fischer |
| 5,318,589 A | 6/1994 | Lichtman |
| 5,337,732 A | 8/1994 | Grundfest et al. |
| 5,339,799 A | 8/1994 | Kami et al. |
| 5,343,385 A | 8/1994 | Joskowicz et al. |
| 5,354,296 A | 10/1994 | Turkel |
| 5,354,314 A | 10/1994 | Hardy et al. |
| 5,355,743 A | 10/1994 | Tesar |
| 5,359,993 A | 11/1994 | Slater et al. |
| 5,369,851 A | 12/1994 | Merkel |
| 5,372,147 A | 12/1994 | Lathrop, Jr. et al. |
| 5,380,338 A | 1/1995 | Christian |
| 5,382,885 A | 1/1995 | Salcudean et al. |
| 5,397,323 A | 3/1995 | Taylor et al. |
| 5,399,951 A | 3/1995 | Lavallee et al. |
| 5,400,267 A | 3/1995 | Denen et al. |
| 5,400,772 A | 3/1995 | LeVahn et al. |
| 5,402,793 A | 4/1995 | Gruner et al. |
| 5,402,801 A | 4/1995 | Taylor |
| 5,403,319 A | 4/1995 | Matsen, III et al. |
| 5,413,573 A | 5/1995 | Koivukangas |
| 5,417,210 A | 5/1995 | Funda et al. |
| 5,427,097 A | 6/1995 | Depp |
| 5,429,142 A | 7/1995 | Szabo et al. |
| 5,433,221 A | 7/1995 | Adair |
| 5,441,042 A | 8/1995 | Putman |
| 5,445,638 A | 8/1995 | Rydell et al. |
| 5,451,368 A | 9/1995 | Jacob |
| 5,457,857 A | 10/1995 | Lam |
| 5,458,132 A | 10/1995 | Yabe et al. |
| 5,480,409 A | 1/1996 | Riza |
| 5,490,524 A | 2/1996 | Williams et al. |

(56) References Cited

U.S. PATENT DOCUMENTS

| | | |
|---|---|---|
| 5,498,230 A | 3/1996 | Adair |
| 5,520,678 A | 5/1996 | Heckele et al. |
| 5,535,973 A | 7/1996 | Bailey et al. |
| 5,562,700 A | 10/1996 | Huitema et al. |
| 5,570,500 A | 11/1996 | Merkel |
| 5,571,110 A | 11/1996 | Matsen, III |
| 5,617,857 A | 4/1997 | Chader et al. |
| 5,624,398 A | 4/1997 | Smith et al. |
| 5,630,431 A | 5/1997 | Taylor |
| 5,631,832 A | 5/1997 | Hagenbuch |
| 5,631,973 A | 5/1997 | Green |
| 5,649,956 A | 7/1997 | Jensen et al. |
| 5,653,705 A | 8/1997 | de la Torre et al. |
| 5,658,077 A | 8/1997 | Hoftman |
| 5,676,673 A | 10/1997 | Ferre et al. |
| 5,678,284 A | 10/1997 | Genero et al. |
| 5,690,635 A | 11/1997 | Matsen, III et al. |
| 5,695,500 A | 12/1997 | Taylor et al. |
| 5,695,501 A | 12/1997 | Carol et al. |
| 5,697,939 A | 12/1997 | Kubota et al. |
| 5,710,870 A | 1/1998 | Ohm et al. |
| 5,716,354 A | 2/1998 | Hluchy |
| 5,732,712 A | 3/1998 | Adair |
| 5,741,210 A | 4/1998 | Dobrovolny |
| 5,749,885 A | 5/1998 | Sjostrom et al. |
| 5,762,458 A | 6/1998 | Wang et al. |
| 5,765,565 A | 6/1998 | Adair |
| 5,779,623 A | 7/1998 | Bonnell |
| 5,784,542 A | 7/1998 | Ohm et al. |
| 5,785,643 A | 7/1998 | Lynn |
| 5,792,044 A | 8/1998 | Foley et al. |
| 5,792,135 A | 8/1998 | Madhani et al. |
| 5,797,900 A | 8/1998 | Madhani et al. |
| 5,800,423 A | 9/1998 | Jensen |
| 5,802,641 A | 9/1998 | Van Steenburg |
| 5,807,377 A | 9/1998 | Madhani et al. |
| 5,807,378 A | 9/1998 | Jensen et al. |
| 5,808,665 A | 9/1998 | Green |
| 5,810,880 A | 9/1998 | Jensen et al. |
| 5,814,038 A | 9/1998 | Jensen et al. |
| 5,817,084 A | 10/1998 | Jensen |
| 5,830,121 A | 11/1998 | Enomoto et al. |
| 5,833,656 A | 11/1998 | Smith et al. |
| 5,849,022 A | 12/1998 | Sakashita et al. |
| 5,853,363 A | 12/1998 | Vought |
| 5,855,583 A | 1/1999 | Wang et al. |
| 5,873,814 A | 2/1999 | Adair |
| 5,876,325 A | 3/1999 | Mizuno et al. |
| 5,876,328 A | 3/1999 | Fox et al. |
| 5,878,193 A | 3/1999 | Wang et al. |
| 5,929,899 A | 7/1999 | Takahashi et al. |
| 5,931,832 A | 8/1999 | Jensen |
| 5,941,889 A | 8/1999 | Cermak |
| 5,951,461 A | 9/1999 | Nyo et al. |
| 5,954,259 A * | 9/1999 | Viola .............. A61B 17/07207 227/176.1 |
| 5,964,780 A | 10/1999 | Balazs |
| 5,970,980 A | 10/1999 | Adair |
| 5,971,997 A | 10/1999 | Guthrie et al. |
| 5,976,122 A | 11/1999 | Madhani et al. |
| 5,992,782 A * | 11/1999 | Goodknight ............. F16D 3/62 242/340 |
| 5,996,889 A | 12/1999 | Fuchs et al. |
| 5,997,471 A | 12/1999 | Gumb et al. |
| 6,024,695 A | 2/2000 | Taylor et al. |
| 6,042,166 A | 3/2000 | Conte |
| 6,056,281 A | 5/2000 | Moilanen et al. |
| 6,063,095 A | 5/2000 | Wang et al. |
| 6,067,869 A * | 5/2000 | Chilla ..................... E05B 77/04 292/336.3 |
| 6,102,044 A | 8/2000 | Naidyhorski |
| 6,102,850 A | 8/2000 | Wang et al. |
| 6,120,433 A | 9/2000 | Mizuno et al. |
| 6,123,080 A | 9/2000 | Mohan et al. |
| 6,132,368 A | 10/2000 | Cooper |
| 6,134,993 A | 10/2000 | Tally |
| 6,149,607 A | 11/2000 | Simpson et al. |
| 6,151,981 A | 11/2000 | Costa |
| 6,152,871 A | 11/2000 | Foley et al. |
| 6,152,920 A | 11/2000 | Thompson et al. |
| 6,167,658 B1 | 1/2001 | Weiner |
| 6,167,884 B1 | 1/2001 | Navis |
| 6,190,399 B1 | 2/2001 | Palmer et al. |
| D438,617 S | 3/2001 | Cooper et al. |
| 6,197,017 B1 | 3/2001 | Brock et al. |
| 6,206,903 B1 | 3/2001 | Ramans |
| 6,208,515 B1 | 3/2001 | Klein |
| D441,076 S | 4/2001 | Cooper et al. |
| D441,862 S | 5/2001 | Cooper et al. |
| 6,231,565 B1 | 5/2001 | Tovey et al. |
| 6,236,880 B1 | 5/2001 | Raylman et al. |
| 6,246,200 B1 | 6/2001 | Blumenkranz et al. |
| D444,555 S | 7/2001 | Cooper et al. |
| 6,259,806 B1 | 7/2001 | Green |
| 6,276,312 B1 | 8/2001 | Summan et al. |
| 6,325,808 B1 | 12/2001 | Bernard et al. |
| 6,327,756 B1 | 12/2001 | Maziere |
| 6,331,181 B1 | 12/2001 | Tierney et al. |
| 6,334,860 B1 | 1/2002 | Dorn |
| 6,346,072 B1 | 2/2002 | Cooper |
| 6,370,411 B1 | 4/2002 | Osadchy et al. |
| 6,394,998 B1 | 5/2002 | Wallace et al. |
| 6,398,726 B1 | 6/2002 | Ramans et al. |
| 6,424,885 B1 | 7/2002 | Niemeyer et al. |
| 6,434,507 B1 | 8/2002 | Clayton et al. |
| 6,451,027 B1 | 9/2002 | Cooper et al. |
| 6,468,265 B1 | 10/2002 | Evans et al. |
| 6,491,701 B2 | 12/2002 | Tierney et al. |
| 6,554,844 B2 | 4/2003 | Lee et al. |
| 6,607,170 B1 | 8/2003 | Hoftman |
| 6,612,310 B2 | 9/2003 | Sklar |
| 6,676,684 B1 * | 1/2004 | Morley et al. ................ 606/205 |
| 6,699,177 B1 | 3/2004 | Wang et al. |
| 6,738,656 B1 | 5/2004 | Ferre et al. |
| 6,770,081 B1 | 8/2004 | Cooper et al. |
| 6,805,453 B2 | 10/2004 | Spetzler et al. |
| 6,862,780 B2 | 3/2005 | Henry |
| 6,866,671 B2 | 3/2005 | Tierney et al. |
| 6,889,116 B2 | 5/2005 | Jinno |
| 6,912,959 B2 | 7/2005 | Kolody et al. |
| 6,936,042 B2 | 8/2005 | Wallace et al. |
| 6,966,104 B2 | 11/2005 | Gregel et al. |
| 7,048,745 B2 | 5/2006 | Tierney et al. |
| 7,074,180 B2 | 7/2006 | Bertolero et al. |
| 7,122,032 B2 | 10/2006 | Shinmura et al. |
| 7,250,028 B2 | 7/2007 | Julian et al. |
| 7,263,501 B2 | 8/2007 | Tirinato et al. |
| 7,320,556 B2 | 1/2008 | Vagn-Erik |
| 7,357,774 B2 | 4/2008 | Cooper |
| 7,395,563 B2 | 7/2008 | Whitmore, III |
| 7,524,320 B2 | 4/2009 | Tierney et al. |
| 7,666,191 B2 | 2/2010 | Orban, III et al. |
| 7,699,855 B2 | 4/2010 | Anderson et al. |
| 7,727,244 B2 | 6/2010 | Orban, III et al. |
| 7,770,859 B2 | 8/2010 | Costabel et al. |
| 7,819,885 B2 | 10/2010 | Cooper |
| 7,907,166 B2 | 3/2011 | Lamprecht et al. |
| 7,918,861 B2 | 4/2011 | Brock et al. |
| 7,963,913 B2 | 6/2011 | Devengenzo et al. |
| 8,105,338 B2 | 1/2012 | Anderson et al. |
| 8,142,447 B2 | 3/2012 | Cooper et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,216,250 B2 | 7/2012 | Orban, III et al. |
| 8,529,582 B2 | 9/2013 | Devengenzo et al. |
| 8,608,773 B2 | 12/2013 | Tierney et al. |
| 8,758,352 B2 | 6/2014 | Cooper et al. |
| 8,998,799 B2 | 4/2015 | Orban, III et al. |
| 8,998,930 B2 | 4/2015 | Orban, III |
| 2002/0045888 A1 | 4/2002 | Ramans et al. |
| 2002/0087048 A1 * | 7/2002 | Brock et al. ................ 600/114 |
| 2002/0091374 A1 | 7/2002 | Cooper |
| 2002/0177754 A1 | 11/2002 | Phillips |

(56) References Cited

U.S. PATENT DOCUMENTS

| | | |
|---|---|---|
| 2003/0006653 A1 | 1/2003 | Kang et al. |
| 2003/0050649 A1 | 3/2003 | Brock et al. |
| 2003/0083673 A1 | 5/2003 | Tierney et al. |
| 2003/0085147 A1 | 5/2003 | Gabriele |
| 2003/0111366 A1 | 6/2003 | Enners |
| 2004/0035334 A1 | 2/2004 | Lohrengel et al. |
| 2004/0049205 A1 | 3/2004 | Lee et al. |
| 2004/0127891 A1 | 7/2004 | Humble et al. |
| 2004/0133189 A1 | 7/2004 | Sakurai |
| 2004/0179754 A1 | 9/2004 | Taheri |
| 2005/0051050 A1 | 3/2005 | Bindra |
| 2005/0149003 A1 | 7/2005 | Tierney et al. |
| 2005/0184207 A1 | 8/2005 | Bertram, III |
| 2005/0222554 A1 | 10/2005 | Wallace et al. |
| 2005/0229937 A1 | 10/2005 | Salvaggio et al. |
| 2005/0240178 A1 | 10/2005 | Morley et al. |
| 2006/0111692 A1 | 5/2006 | Hlavka et al. |
| 2006/0113208 A1 | 6/2006 | Clark et al. |
| 2006/0161136 A1 | 7/2006 | Anderson et al. |
| 2006/0161137 A1 | 7/2006 | Orban, III |
| 2006/0161138 A1 | 7/2006 | Orban, III |
| 2006/0167440 A1 | 7/2006 | Cooper et al. |
| 2006/0235436 A1 | 10/2006 | Anderson et al. |
| 2006/0276775 A1 | 12/2006 | Rosenberg et al. |
| 2007/0043338 A1 | 2/2007 | Moll et al. |
| 2007/0070157 A1 | 3/2007 | Wang |
| 2007/0137371 A1 | 6/2007 | Devengenzo et al. |
| 2007/0137372 A1 | 6/2007 | Devengenzo et al. |
| 2007/0142824 A1 | 6/2007 | Devengenzo et al. |
| 2007/0142969 A1 | 6/2007 | Devengenzo et al. |
| 2007/0185376 A1 | 8/2007 | Wilson et al. |
| 2007/0239172 A1 | 10/2007 | Lee et al. |
| 2009/0030429 A1 | 1/2009 | Madhani et al. |
| 2009/0247819 A1 | 10/2009 | Wilson et al. |
| 2011/0028990 A1 | 2/2011 | Cooper |
| 2011/0066161 A1 | 3/2011 | Cooper |
| 2012/0209291 A1 | 8/2012 | Anderson et al. |
| 2012/0232566 A1 | 9/2012 | Orban, III et al. |
| 2012/0239060 A1 | 9/2012 | Orban, III |
| 2012/0247489 A1 | 10/2012 | Orban, III et al. |
| 2014/0180310 A1 | 6/2014 | Blumenkranz et al. |
| 2015/0173841 A1 | 6/2015 | Orban, III |

FOREIGN PATENT DOCUMENTS

| | | |
|---|---|---|
| DE | 19950440 A1 | 11/2001 |
| DE | 102007030856 B3 | 4/2009 |
| EP | 0606531 | 7/1994 |
| EP | 0705571 | 4/1996 |
| EP | 1321106 A1 | 6/2003 |
| EP | 1439026 | 7/2004 |
| EP | 1889576 | 2/2008 |
| EP | 2263594 | 12/2010 |
| EP | 2263595 | 12/2010 |
| GB | 2366319 A | 3/2002 |
| JP | S59190214 U | 12/1984 |
| JP | H01280449 A | 11/1989 |
| JP | H03121064 A | 5/1991 |
| JP | H03143438 A | 6/1991 |
| JP | 4092656 A | 3/1992 |
| JP | H0661205 U | 8/1994 |
| JP | H06261911 A | 9/1994 |
| JP | H06269461 A | 9/1994 |
| JP | 07194610 A | 8/1995 |
| JP | H07241300 A | 9/1995 |
| JP | H07509637 A | 10/1995 |
| JP | H0884735 A | 4/1996 |
| JP | 8182684 | 7/1996 |
| JP | H08215211 A | 8/1996 |
| JP | H08224248 A | 9/1996 |
| JP | H08280697 A | 10/1996 |
| JP | H08509886 A | 10/1996 |
| JP | H11507252 A | 6/1999 |
| JP | 2000505328 A | 5/2000 |
| JP | 2002500524 A | 1/2002 |
| JP | 2003061969 | 3/2003 |
| JP | 2003235868 A | 8/2003 |
| JP | 2003325543 A | 11/2003 |
| JP | 2004000334 A | 1/2004 |
| JP | 2004097533 A | 4/2004 |
| JP | 2004244091 A | 9/2004 |
| JP | 2005524442 A | 8/2005 |
| WO | WO9220295 | 11/1992 |
| WO | WO-9313916 A1 | 7/1993 |
| WO | WO-9320770 A2 | 10/1993 |
| WO | WO9403113 | 2/1994 |
| WO | WO9414129 | 6/1994 |
| WO | WO9426167 | 11/1994 |
| WO | WO-9503001 A1 | 2/1995 |
| WO | WO-9505780 A1 | 3/1995 |
| WO | WO-9516396 A1 | 6/1995 |
| WO | WO-9530964 A1 | 11/1995 |
| WO | WO-9608209 A2 | 3/1996 |
| WO | WO-9639944 A1 | 12/1996 |
| WO | WO-9712554 A1 | 4/1997 |
| WO | WO-9728734 A1 | 8/1997 |
| WO | WO-9729690 A1 | 8/1997 |
| WO | WO-9729710 A1 | 8/1997 |
| WO | WO-9825666 A1 | 6/1998 |
| WO | WO-9950721 A1 | 10/1999 |
| WO | WO-0001304 A1 | 1/2000 |
| WO | WO0033755 | 6/2000 |
| WO | WO-03092523 A1 | 11/2003 |

OTHER PUBLICATIONS

EP11156085.0 European Search Report, mailed May 31, 2011, 7 pages.

European Search Report for Application No. EP11156082, mailed Jul. 1, 2011, 11 pages.

European Search Report for Application No. EP11156083, mailed on Feb. 28, 2012, 8 pages.

European Search Report for Application No. EP11156087, mailed on Jun. 21, 2011, 9 pages.

European Search Report for Application No. EP11156090, mailed on Jun. 21, 2011, 12 pages.

European Search Report for Application No. EP11156097, mailed on Jul. 18, 2011, 10 pages.

Extended European Search Report for Application No. EP09172378, mailed on Jul. 27, 2010, 10 pages.

International Search Report for application No. PCT/US99/29045, Mailed on May 9, 2000, 1 page.

Madhani, Akhil J. et al., "The black falcon: A teleoperated surgical instrument for minimally invasive surgery," IEEE/RSJ Int. Conf. on Intelligent Robots and Systems (IROS) Victoria B.C. Canada ), 1998, pp. 936-944, vol. 2, IEEE.

Moyer, Thomas H., "The design for an integrated hand and wrist mechanism," Masters Thesis, Feb. 1992, 106 pages, Massachusetts Institute of Technology.

Neisius B. et al., "Robotic manipulator for endoscopic handling of surgical effectors and cameras," 1st Intl. Symposium on Medical Robotics and Computer Assisted Surgery, 1994, pp. 169-176, vol. 2.

Partial European Search Report for Application No. EP07119840, mailed on Jun. 23, 2008, 17 pages.

Partial European Search Report for Application No. EP10182603, mailed on Apr. 18, 2012, 9 pages.

Partial European Search Report for Application No. EP10182720, mailed on Apr. 20, 2012, 6 pages.

Partial European Search Report for Application No. EP10182750, mailed on May 11, 2012, 10 pages.

Partial European Search Report for Application No. EP10182798, mailed on May 4, 2012, 9 pages.

Salisbury, Kenneth J., "Kinematic and force analysis of articulated hands," Department of Computer Science Stanford University Report No. STAN CS 89 921, 1982, Chapter 9, pp. 67-77.

Supplementary European Search Report for Application No. EP99968468, mailed on Aug. 13, 2004, 6 pages.

Task 2: Miniature end effector—A preliminary design, pp. 32-47, no date.

(56) References Cited

OTHER PUBLICATIONS

Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited, Chapter 5,7,8,9.
EP Search Report, Application No. EP10182921, Mar. 7, 2013, 7 pgs.
EP Search Report (Extended) Application No. EP10182922, Feb. 6, 2013, 7 pgs.
FR Preliminary Search Report, Application No. 1255442, Feb. 8, 2013, 12 pgs.
Green P.S., et al., "Telepresence Surgery," IEEE Engineering in Medicine and Biology Magazine, IEEE Service Center, Pisacataway, NJ, US, May 1, 1995, vol. 14(3), pp. 324-329, XP000505090.
JP Application No. 2008-547535, Office Action, Dec. 19, 2001, 7 pgs.
PCT/US06/48744, International Search Report and Written Opinion, May 8, 2007, 11 pgs.
U.S. Appl. No. 60/033,321, filed Dec. 12, 1996, Cooper, Thomas G.
U.S. Appl. No. 60/752,755, filed Dec. 20, 2005, Devengenzo, et al.
Vertut, Jean and Phillipe Coiffet, Robot Technology; Teleoperation and Robotics Evolution and Development, English translation, Prentice-Hall, Inc., Inglewood Cliffs, NJ, USA, 1986, vol. 3A, 332 pgs.
Extended European Search Report for Application No. EP10182603, mailed on Sep. 23, 2014, 17 pages.
Extended European Search Report for Application No. EP10182720, mailed on Sep. 23, 2014, 15 pages.
Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.
U.S. Appl. No. 08/517,053, filed Aug. 21, 1995.
U.S. Appl. No. 60/752,472, filed Dec. 20, 2005.
U.S. Appl. No. 60/986,914, filed Nov. 9, 2007.
European Search Report for Application No. EP09172358, mailed on Jan. 17, 2012, 6 pages.
European Search Report for Application No. EP10182919, mailed Feb. 14, 2013, 9 pages.
European Search Report for Application No. EP10182920, mailed on Feb. 11, 2013, 5 pages.
Extended European Search Report for Application No. EP11156882, mailed on May 19, 2011, 7 pages.
Extended European Search Report for Application No. EP12192481, mailed on Nov. 13, 2013, 8 pages.
FR0611140 Preliminary Search Report Notification and Written Opinion, dated Aug. 4, 2009, 5 pages.
FR0611141 Preliminary Search Report Notification and Written Opinion, dated Aug. 4, 2009, 5 pages.
International Search Report and Written Opinion for Application No. PCT/US2008/082628, mailed Jun. 16, 2009, 9 pages.
International Search Report for application No. PCT/US97/22035, Mailed on Apr. 21, 1998, 2 pages.
PCT/US06/37432 International Search Report, mailed Dec. 15, 2006, 4 pages.
PCT/US06/37432 Written Opinion of the International Search Authority, mailed Dec. 15, 2006, 7 pages.
PCT/US06/37434 International Search Report and Written Opinion of the International Search Authority, mailed Feb. 19, 2007, 12 pages.
PCT/US06/62363 International Search Report, mailed Dec. 14, 2007, 2 pages.
PCT/US06/62363 Written Opinion of the International Search Authority, mailed Dec. 14, 2007, 5 pages.
PCT/US06/62364 International Search Report, mailed Jun. 12, 2006, 3 pages.
PCT/US06/62364 Written Opinion of the International Search Authority, mailed Jun. 12, 2006, 4 pages.
Sabatini, A. M. et al., "Force Feedback Based Telemicromanipulation for Robot Surgery on Soft Tissue," IEEE Engineering in Medicine and Biology Society 11th Annual International Conference, 1989, pp. 890-891, vol. 3, IEEE.
Supplementary European Search Report for Application No. EP97949717, mailed on Mar. 7, 2008, 3 pages.
Office Action mailed Oct. 24, 2014 for Japanese Application No. 2013231856 filed Nov. 8, 2013, 5 pages.
Office Action mailed Jun. 4, 2014 for Japanese Application No. 20120219670 filed Oct. 1, 2012, 8 pages.
Supplementary Partial European Search Report for Application No. 20100182798, mailed on Mar. 20, 2015, 5 pages.
Extended European Search Report for Application No. 15174908.2, mailed on Dec. 7, 2015, 5 pages.
Office Action mailed Mar. 29, 2016 for Japanese Application No. 2014-179860 filed Sep. 4, 2014, 10 pages.

* cited by examiner

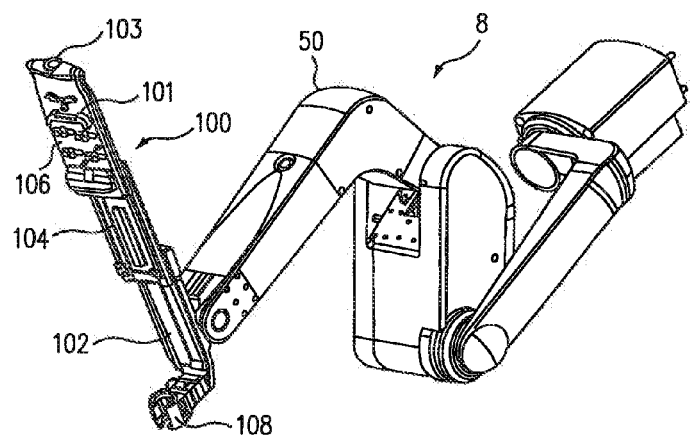 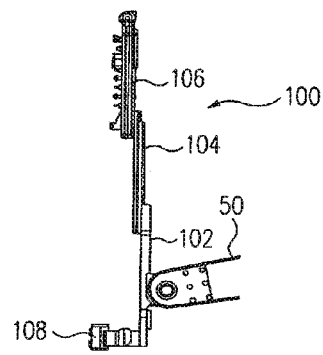
FIG. 5B    FIG. 5B1
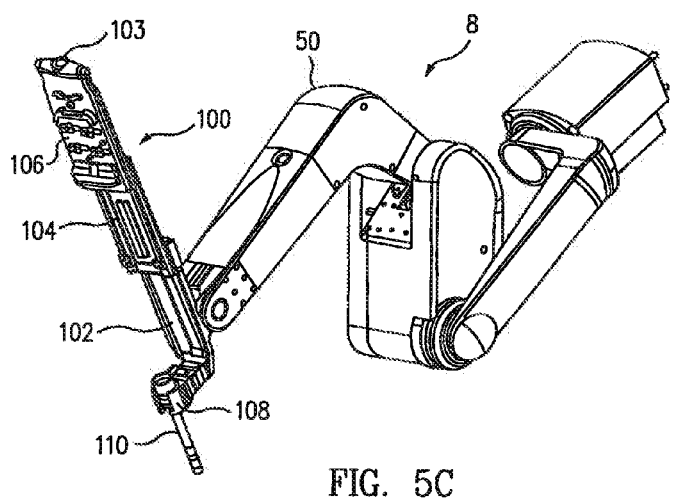 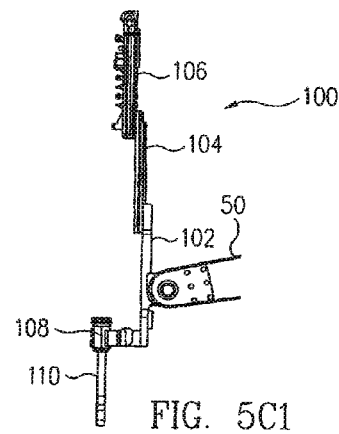
FIG. 5C    FIG. 5C1

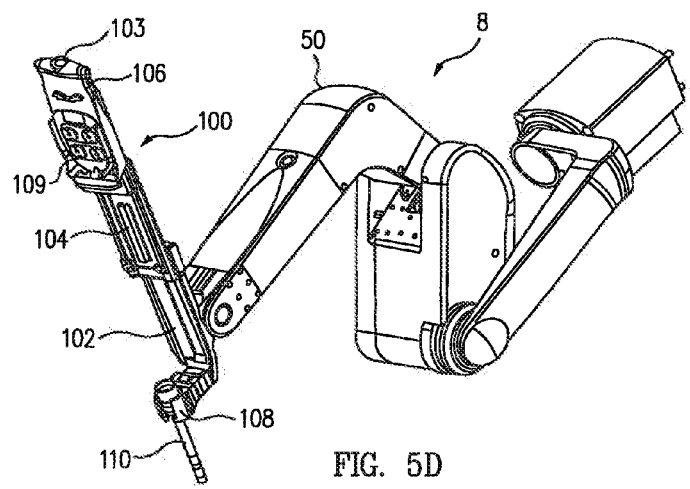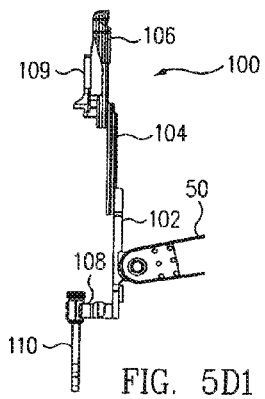
FIG. 5D  FIG. 5D1
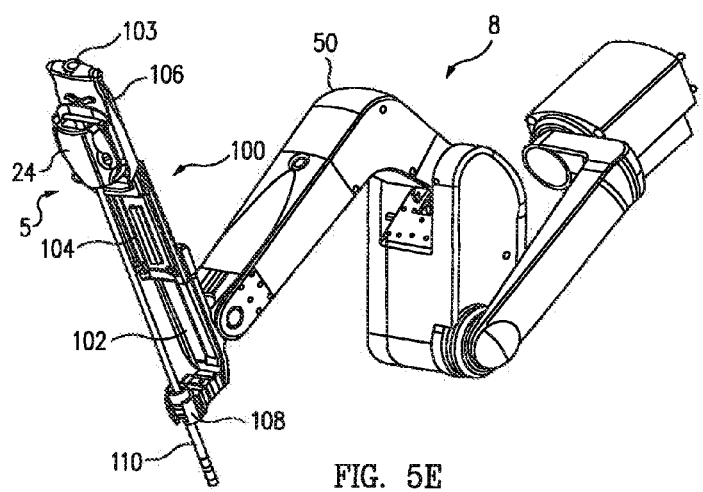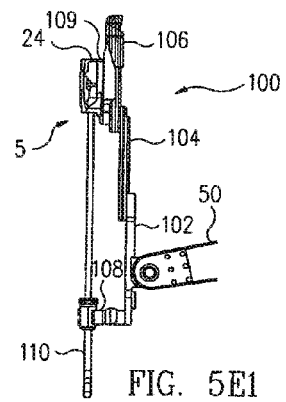
FIG. 5E  FIG. 5E1

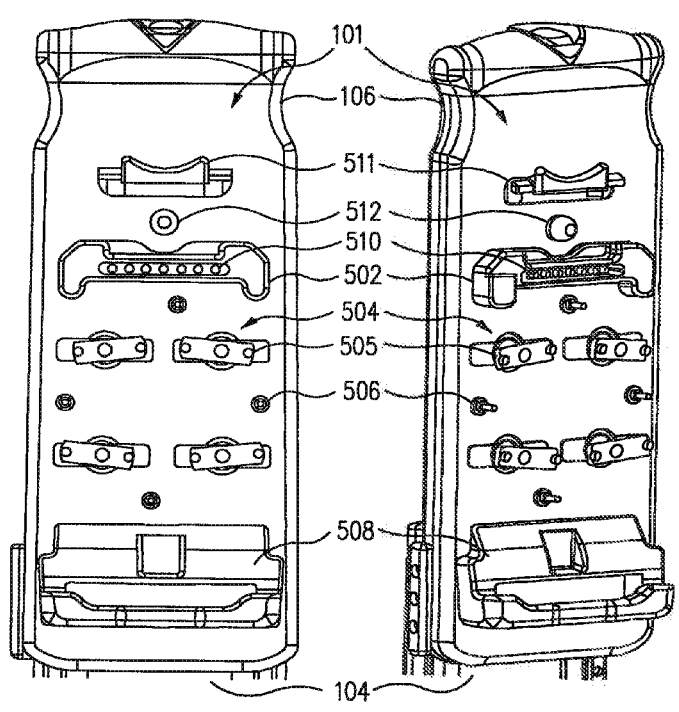
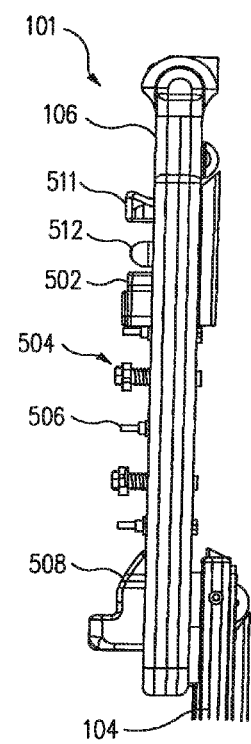
FIG. 6A  FIG. 6B  FIG. 6C

INSTRUMENT INTERFACE OF A ROBOTIC SURGICAL SYSTEM

CROSS-REFERENCE TO RELATED APPLICATIONS

This application is a continuation of U.S. patent application Ser. No. 13/112,452, filed May 20, 2011, entitled "Instrument Interface of a Robotic Surgical System," which is a continuation of U.S. patent application Ser. No. 11/613,695, now U.S. Pat. No. 7,963,913, filed Dec. 20, 2006, entitled "Instrument Interface of a Robotic Surgical System", which application claims the benefit of U.S. Provisional Application No. 60/752,755, filed Dec. 20, 2005, the full disclosures of which (including all references incorporated by reference therein) are incorporated by reference herein for all purposes.

This application is a continuation of U.S. patent application Ser. No. 13/112,452, filed May 20, 2011, entitled "Instrument Interface of a Robotic Surgical System," which is a continuation of U.S. patent application Ser. No. 11/613,695, now U.S. Pat. No. 7,963,913, filed Dec. 20, 2006, entitled "Instrument Interface of a Robotic Surgical System", which is a continuation-in-part of pending U.S. patent application Ser. No. 11/314,040, filed Dec. 20, 2005, now U.S. Pat. No. 7,666,191, which is a continuation-in-part of pending U.S. patent application Ser. No. 10/922,346, filed Aug. 19, 2004, now U.S. Pat. No. 7,357,774, which is a continuation of U.S. patent application Ser. No. 10/004,399, filed Oct. 30, 2001, now abandoned, which is a continuation of U.S. patent application Ser. No. 09/406,360, filed Sep. 28, 1999, now U.S. Pat. No. 6,346,072, which is a continuation of U.S. patent application Ser. No. 08/975,617, filed Nov. 21, 1997, now U.S. Pat. No. 6,132,368, which claimed priority to U.S. Provisional Application No. 60/033,321, filed Dec. 12, 1996, the full disclosures of which are hereby incorporated by reference for all purposes.

This application is related to U.S. application Ser. No. 11/613,578, filed Dec. 20, 2006, entitled "Cable Tensioning In A Robotic Surgical System", U.S. application Ser. No. 11/613,800, now U.S. Pat. No. 8,182,470, filed Dec. 20, 2006, entitled "Telescoping Insertion Axis Of A Robotic Surgical System", U.S. application Ser. No. 11/556,484, now U.S. Pat. No. 8,273,076, filed Nov. 3, 2006, entitled "Indicator For Tool State and Communication In a Multi-Arm Robotic Telesurgery", U.S. application Ser. No. 11/613,915 now U.S. Pat. No. 7,955,322, filed Dec. 20, 2006, entitled "Wireless Communication In A Robotic Surgical System", and U.S. application Ser. No. 11/395,418, filed Mar. 31, 2006, entitled "Sterile Surgical Adaptor", now U.S. Pat. No. 7,699,855, the full disclosures of which (including all references incorporated by reference therein) are incorporated by reference herein for all purposes.

TECHNICAL FIELD

The present invention is generally related to medical and/or robotic devices, systems, and methods.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, may be reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and to avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servomechanically operated instruments.

In robotically-assisted surgery, the surgeon typically operates a master controller to control the motion of surgical instruments at the surgical site from a location that may be remote from the patient (e.g., across the operating room, in a different room, or a completely different building from the patient). The master controller usually includes one or more hand input devices, such as hand-held wrist gimbals, joysticks, exoskeletal gloves or the like, which are operatively coupled to the surgical instruments that are releasably coupled to a patient side surgical manipulator ("the slave"). The master controller controls the instruments' position, orientation, and articulation at the surgical site. The slave is an electro mechanical assembly which includes a plurality of arms, joints, linkages, servo motors, etc. that are connected together to support and control the surgical instruments. In a surgical procedure, the surgical instruments (including an endoscope) may be introduced directly into an open surgical site or more typically through trocar sleeves into a body cavity. Depending on a surgical procedure, there are available a variety of surgical instruments, such as tissue graspers, needle drivers, electrosurgical cautery probes, etc., to perform various functions for the surgeon, e.g., holding or driving a needle, suturing, grasping a blood vessel, or dissecting, cauterizing or coagulating tissue.

A surgical manipulator assembly may be said to be divided into three main components that include a non-sterile drive and control component, a sterilizable end effector or surgical tool/instrument, and an intermediate connector component. The intermediate connector component includes mechanical elements for coupling the surgical tool with the drive and control component, and for transferring motion from the drive component to the surgical tool.

A challenge with telerobotic surgery systems is that a surgeon will typically employ a large number of different surgical instruments/tools during a procedure. Since the number of manipulator arms is limited due to space constraints and cost, many of these surgical instruments will be attached and detached from the manipulator arm a number of times during an operation.

While telesurgical systems, devices, and methods have proven highly effective and advantageous, still further improvements would be desirable. In general, it would be desirable to provide an improved instrument interface on the manipulator arm to minimize instrument exchange time and difficulty during the surgical procedure.

SUMMARY

In accordance with an embodiment of the present invention, an instrument interface of a robotic manipulator is provided, the instrument interface including a spring-loaded input for providing axial load and torque to a sterile adaptor capable of operably coupling an instrument. The instrument interface may further include a spring plunger and a spring-loaded release lever.

In accordance with another embodiment of the present invention, a robotic surgical manipulator system is provided, the system comprising a manipulator assembly, including a base link operably coupled to a distal end of a manipulator arm, and a carriage link movably coupled to the base link along a lengthwise axis, the carriage link including an instrument interface as described above. The system further includes an instrument operably coupled to the carriage link via the instrument interface, and a processor operably coupled to the manipulator assembly for sensing the instrument and/or sterile adaptor.

Advantageously, the present invention provides for simple and efficient installment and/or engagement of an instrument sterile adaptor (ISA) while enabling a cost-effective and disposable design for the ISA and a sterile barrier. Other advantages of the invention are provided.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIGS. 5A-5E and 5B1-5E1 are perspective views and respective side views of a manipulator including a telescopic insertion axis in accordance with an embodiment of the present invention.

FIGS. 6A-6E illustrate different views of instrument interface components of the carriage link in accordance with an embodiment of the present invention.

Figure 1:
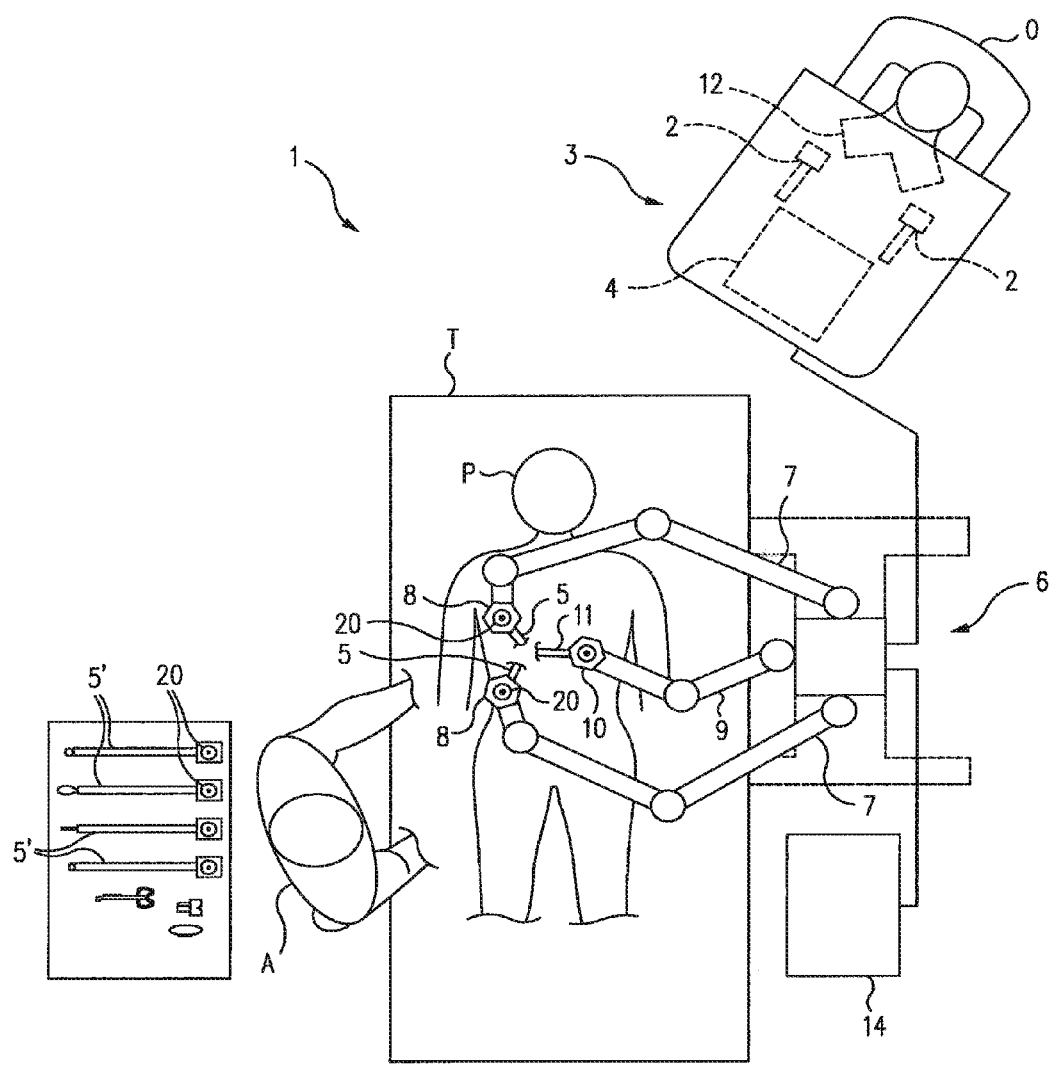
FIG. 1 is a schematic plan view of a portion of an operating theater illustrating a robotic surgical system, including a master surgeon console or workstation for inputting a surgical procedure and a robotic manipulator system for robotically moving surgical instruments at a surgical site within a patient.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention generally provides an improved robotic insertion axis, system, and method for inserting an instrument, and in particular includes a telescopic insertion axis for providing greater stiffness and strength, a larger range of motion, and improved visibility of the surgical field.

The present invention is particularly useful as part of a telerobotic surgical system that allows the surgeon to manipulate the surgical instruments through a servomechanism at a location remote from the patient. One example of a robotic surgical system is the da Vinci® S™ surgical system available from Intuitive Surgical, Inc. of Sunnyvale, Calif. A User's Guide for the da Vinci® S™ surgical system is available from Intuitive Surgical, Inc. and is incorporated by reference herein for all purposes.

Figure 2A:
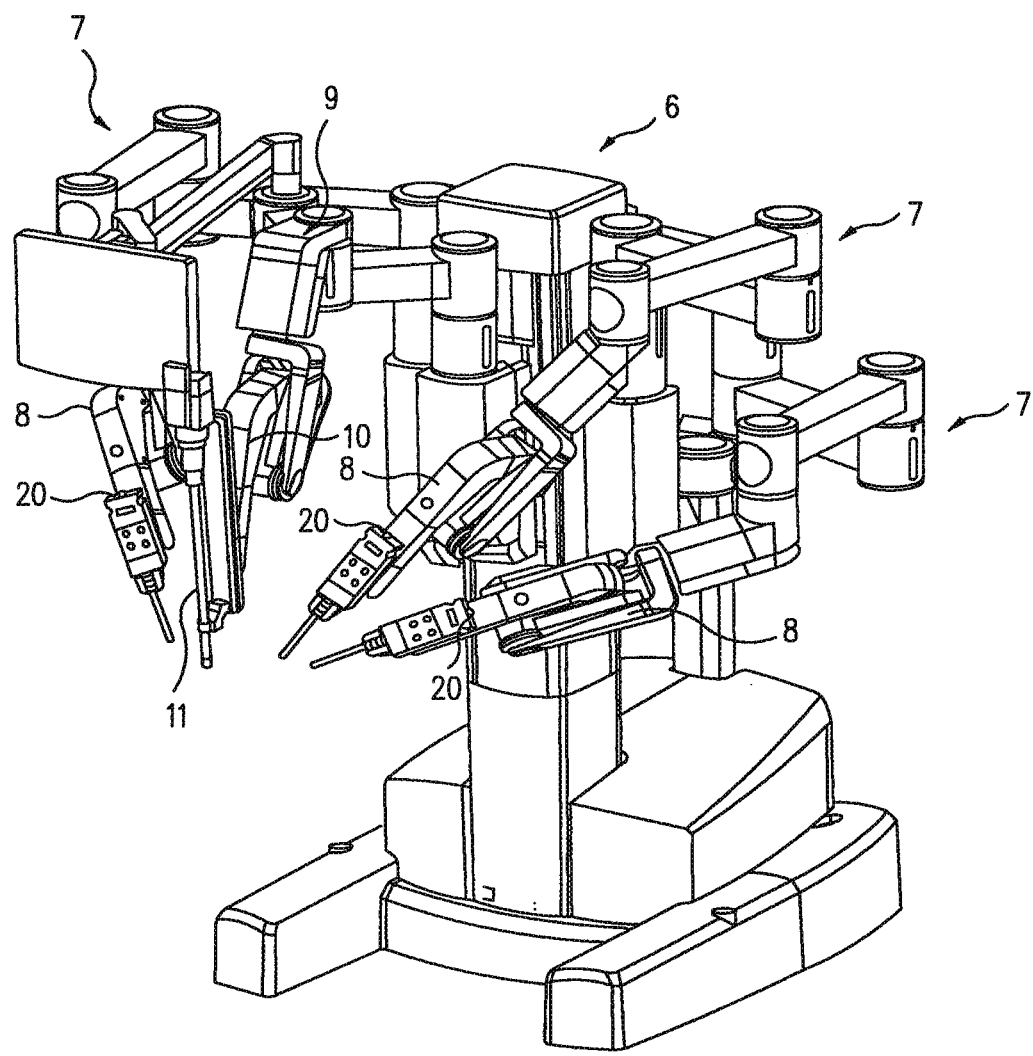
FIGS. 2A and 2B illustrate a perspective view and a front view, respectively, of an embodiment of a manipulator system, including positioning linkages or set up joints which allow a patient side robotic manipulator and/or an endoscope or camera robotic manipulator to be pre-configured for surgery.
Figure 2B:
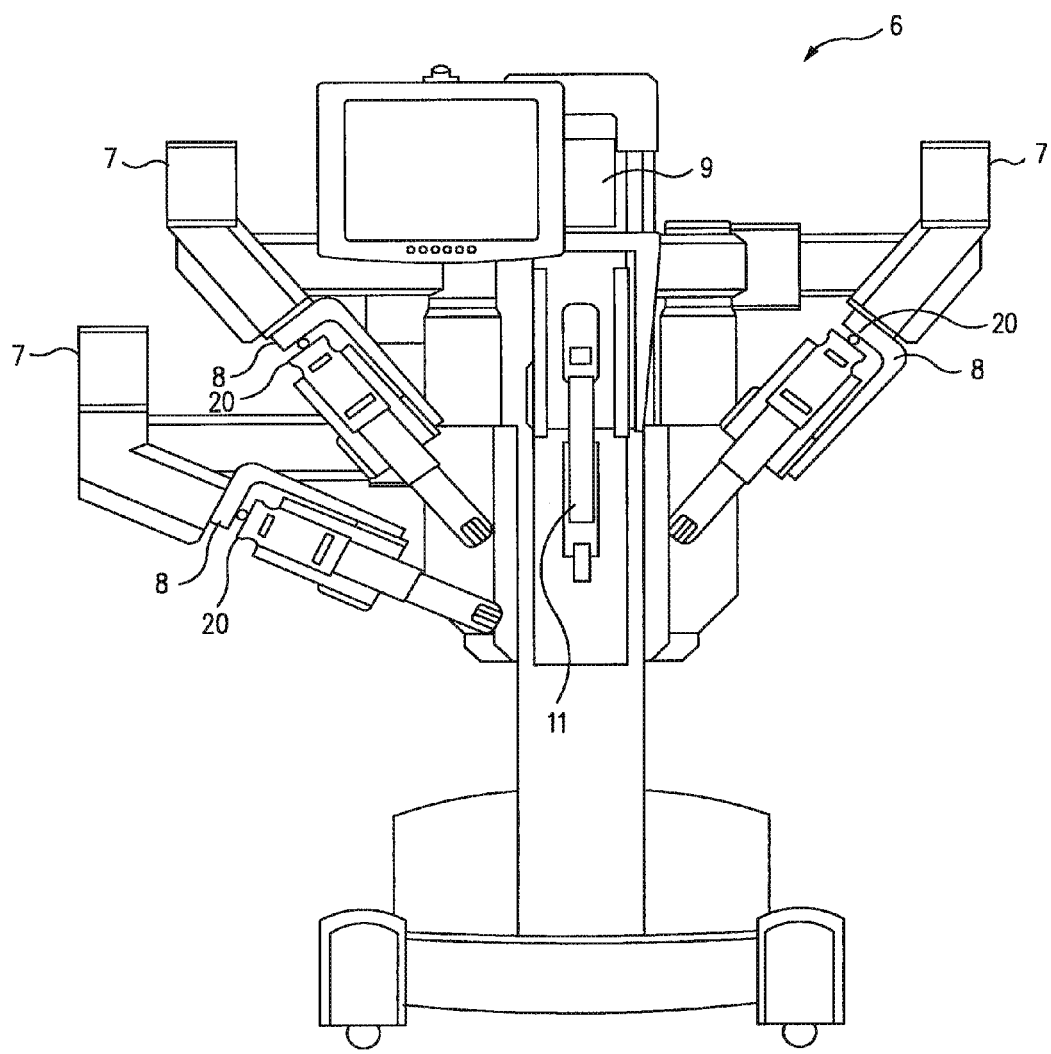
Figure 3:
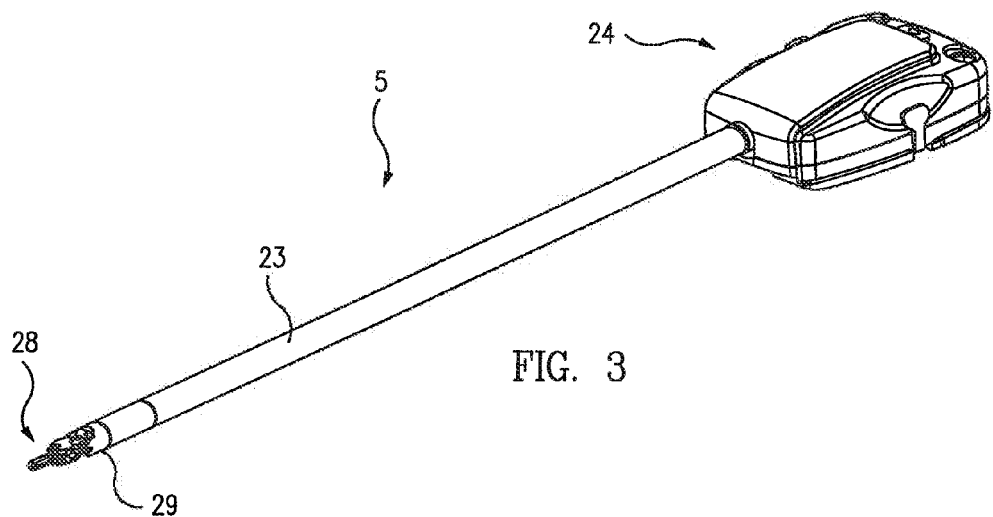
FIG. 3 is a perspective view of an example of a surgical instrument for use in the system of FIG. 1.

FIGS. 1-3 illustrate components of a robotic surgical system 1 for performing minimally invasive robotic surgery. System 1 is similar to that described in more detail in U.S. Pat. No. 6,246,200, the full disclosure of which is incorporated herein by reference. A system operator O (generally a surgeon) performs a minimally invasive surgical procedure on a patient P lying on an operating table T. The system operator O sees images presented by display 12 and manipulates one or more input devices or masters 2 at a surgeon's console 3. In response to the surgeon's input commands, a computer processor 4 of console 3 directs movement of surgical instruments or tools 5, effecting servomechanical movement of the instruments via a robotic patient-side manipulator system 6 (a cart-based system in this example)

including joints, linkages, and manipulator arms each having a telescopic insertion axis. In one embodiment, processor 4 correlates the movement of the end effectors of tools 5 so that the motions of the end effectors follow the movements of the input devices in the hands of the system operator O.

Processor 4 will typically include data processing hardware and software, with the software typically comprising machine-readable code. The machine-readable code will embody software programming instructions to implement some or all of the methods described herein. While processor 4 is shown as a single block in the simplified schematic of FIG. 1, the processor may comprise a number of data processing circuits, with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein.

In one example, manipulator system 6 includes at least four robotic manipulator assemblies. Three linkages 7 (mounted at the sides of the cart in this example) support and position manipulators 8 with linkages 7 in general supporting a base of the manipulators 8 at a fixed location during at least a portion of the surgical procedure. Manipulators 8 move surgical tools 5 for robotic manipulation of tissues. One additional linkage 9 (mounted at the center of the cart in this example) supports and positions manipulator 10 which controls the motion of an endoscope/camera probe 11 to capture an image (preferably stereoscopic) of the internal surgical site. The fixable portion of positioning linkages 7, 9 of the patient-side system is sometimes referred to herein as a "set-up arm".

In one example, the image of the internal surgical site is shown to operator O by a stereoscopic display 12 in surgeon's console 3. The internal surgical site is simultaneously shown to assistant A by an assistance display 14.

Assistant A assists in pre-positioning manipulator assemblies 8 and 10 relative to patient P using set-up linkage arms 7, 9; in swapping tools 5 from one or more of the surgical manipulators for alternative surgical tools or instruments 5'; in operating related non-robotic medical instruments and equipment; in manually moving a manipulator assembly so that the associated tool accesses the internal surgical site through a different aperture, and the like.

In general terms, the linkages 7, 9 are used primarily during set-up of patient-side system 6, and typically remain in a fixed configuration during at least a portion of a surgical procedure. Manipulators 8, 10 each comprise a driven linkage which is actively articulated under the direction of surgeon's console 3. Although one or more of the joints of the set-up arm may optionally be driven and robotically controlled, at least some of the set-up arm joints may be configured for manual positioning by assistant A.

Some of the manipulators include a telescopic insertion axis 100 in accordance with an embodiment of the present invention, although in other embodiments, all of the manipulators may include a telescopic insertion axis 100. Telescopic insertion axis 100 allows for movement of mounted instrument 5, via three operably coupled links, with improved stiffness and strength compared to previous designs, a larger range of motion, and improved dynamic performance and visibility proximate the surgical field for system users (in addition to other advantages), as is described in greater detail below.

For convenience, a manipulator such as manipulator 8 that is supporting a surgical tool used to manipulate tissues is sometimes referred to as a patient-side manipulator (PSM), while a manipulator 10 which controls an image capture or data acquisition device such as endoscope 11 may be referred to as an endoscope-camera manipulator (ECM). The manipulators may optionally actuate, maneuver and control a wide variety of instruments or tools, image capture devices, and the like which are useful for surgery.

Figure 6D:
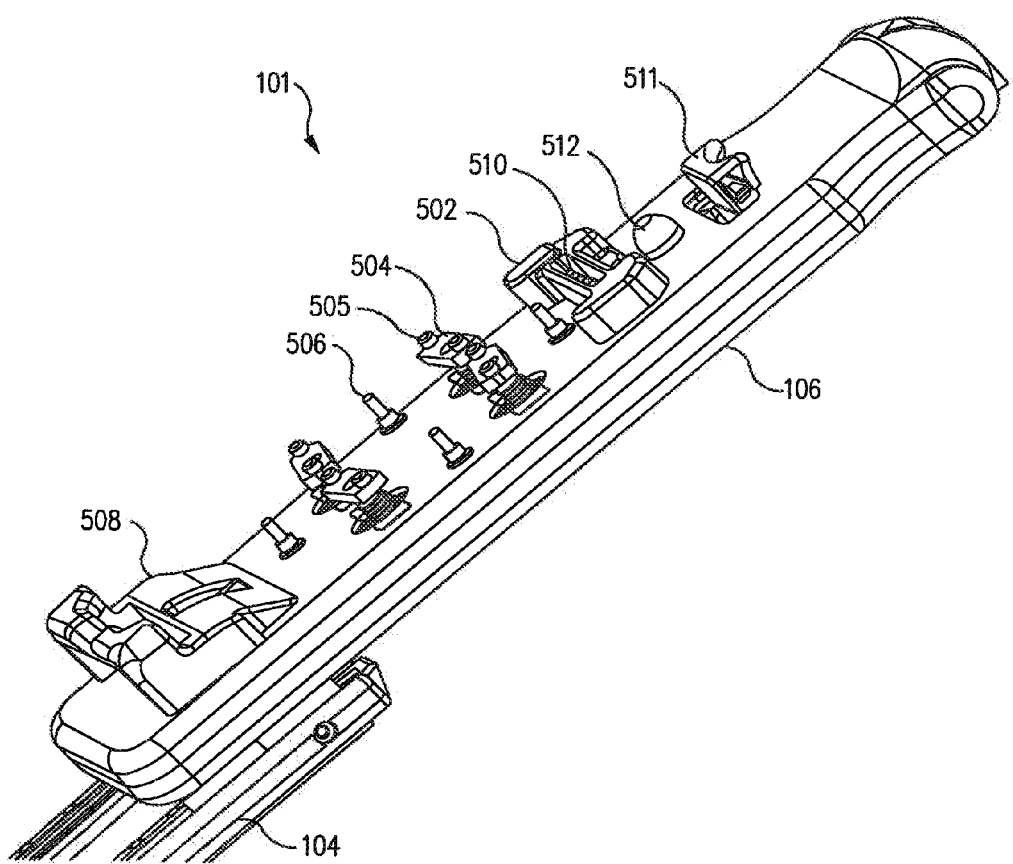
Figure 6E:
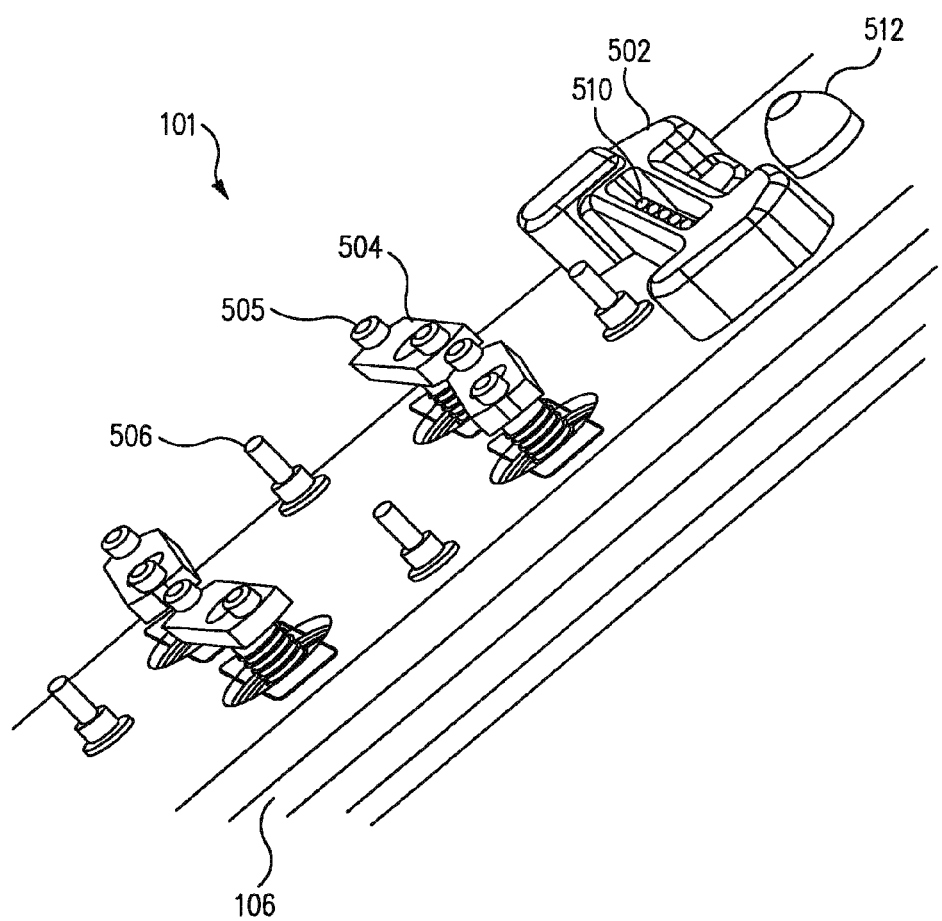

Instruments 5 and endoscope 11 may be manually positioned when setting up for a surgical procedure, when reconfiguring the manipulator system 6 for a different phase of a surgical procedure, when removing and replacing an instrument with an alternate instrument 5', and the like. During such manual reconfiguring of the manipulator assembly by assistant A, the manipulator assembly may be placed in a different mode than is used during master/slave telesurgery, with the manually repositionable mode sometimes being referred to as a clutch mode. The manipulator assembly may change between the tissue manipulation mode and the clutch mode in response to an input such as pushing a button or switch on manipulator 8 (e.g., a clutch button/switch 103 in FIGS. 6A-6C), or some other component to the manipulator assembly, thereby allowing assistant A to change the manipulator mode.

As can be seen in FIGS. 1 and 2A-2B, indicators 20 may be disposed on a manipulator assembly. In this embodiment, indicators 20 are disposed on manipulators 8 near the interface between the manipulators and their mounted tools 5. In alternative embodiments, indicators 20 may instead be disposed on set-up joints 7, 9, on tools 5, elsewhere on manipulators 8, 10, or the like. An example of an indicator is disclosed in U.S. application Ser. No. 11/556,484, filed Nov. 3, 2006, the full disclosure of which (including all references incorporated by reference therein) is incorporated by reference herein for all purposes.

FIG. 3 illustrates a perspective view of an articulated surgical tool or instrument 5. Tool 5 has a proximal housing 24 which interfaces with a tool holder or instrument interface of the manipulator, generally providing a quick release mounting engagement through a sterile adapter or interface, an example of which is disclosed in U.S. patent application Ser. No. 11/314,040, filed Dec. 20, 2005, now U.S. Pat. No. 7,666,191, and U.S. patent application Ser. No. 11/395,418, filed Mar. 31, 2006, now U.S. Pat. No. 7,699,855, which are incorporated by reference herein for all purposes. Tool 5 includes an elongated shaft 23 supporting an end effector 28 relative to proximal housing 24. Proximal housing 24 accepts and transmits drive signals and drive motion between the manipulator 8 and the end effector 28. An articulated wrist 29 may provide two degrees of freedom of motion between end effector 28 and shaft 23, and the shaft may be rotatable relative to proximal housing 24 about the axis of the shaft so as to provide the end effector 28 with three orientational degrees of freedom within the patient's body.

The surgical tool may include a variety of articulated end effectors, such as jaws, scissors, graspers, needle holders, micro-dissectors, staple appliers, tackers, suction irrigation tools, and clip appliers, that may be driven by wire links, eccentric cams, push-rods, or other mechanisms. In addition, the surgical tool may comprise a non-articulated instrument, such as cutting blades, probes, irrigators, catheters or suction orifices. Alternatively, the surgical tool may comprise an electrosurgical probe for ablating, resecting, cutting or coagulating tissue. Examples of applicable adaptors, tools or instruments, and accessories are described in U.S. Pat. Nos.

6,331,181, 6,491,701, and 6,770,081, the full, disclosures of which (including disclosures incorporated by reference therein) are incorporated by reference herein for all purposes. Applicable surgical instruments are also commercially available from Intuitive Surgical, Inc. of Sunnyvale, Calif.

Figure 4:
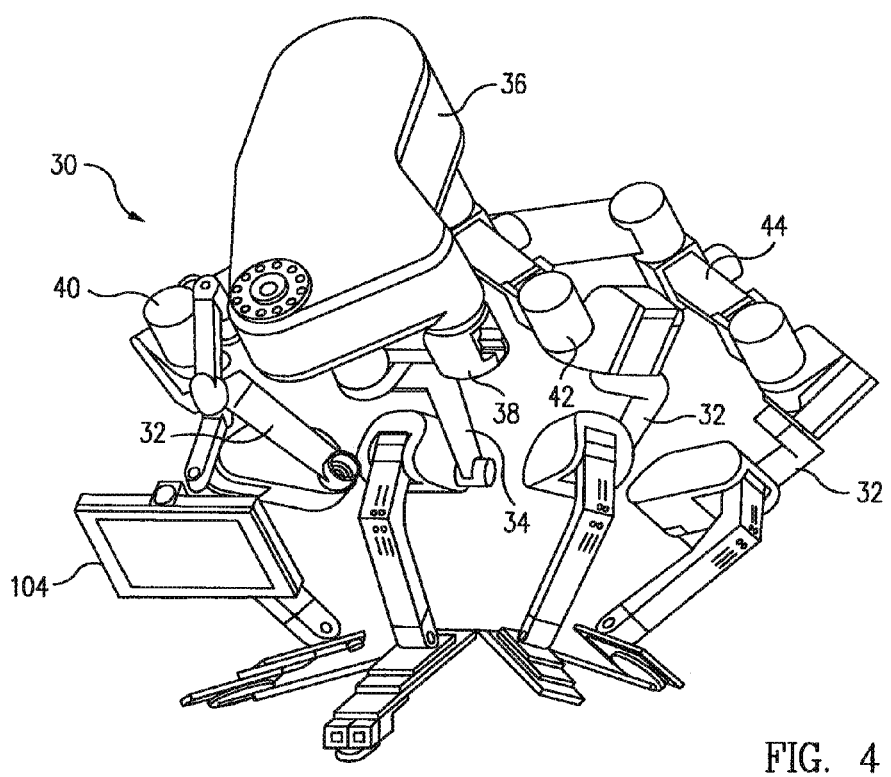
FIG. 4 is a perspective from above of an alternative manipulator system including a plurality of positioning linkages, each supporting a manipulator arm.

Referring now to FIG. 4, a perspective view is illustrated of an alternative modular manipulator support assembly 30 that may be mounted to a ceiling of an operating room. The modular manipulator support 30 aligns and supports a robotic manipulator system relative to a set of desired surgical incision sites in a patient's body. Modular manipulator support 30 generally includes an orientating platform 36 and a plurality of configurable set-up linkage arms 38, 40, 42, 44 that may be coupled to the orienting platform. Each arm movably supports an associated manipulator 32, 34, which in turn movably supports an associated tool or an image capture device. Orienting platform 36 also supports an assistant display 104, which may be used for set-up, instrument changes, viewing of the procedure, and the like. The structures and use of any of the components of modular manipulator support assembly 30 are analogous to those described above regarding manipulator system 6, and are more fully described in co-pending U.S. patent application Ser. No. 11/043,688, filed on Jan. 24, 2005, and entitled "Modular Manipulator Support For Robotic Surgery", the full disclosure of which is incorporated herein by reference. As generally described above, each manipulator 32, 34 of modular manipulator support 30 may also include an insertion axis 100.

Figure 5A:
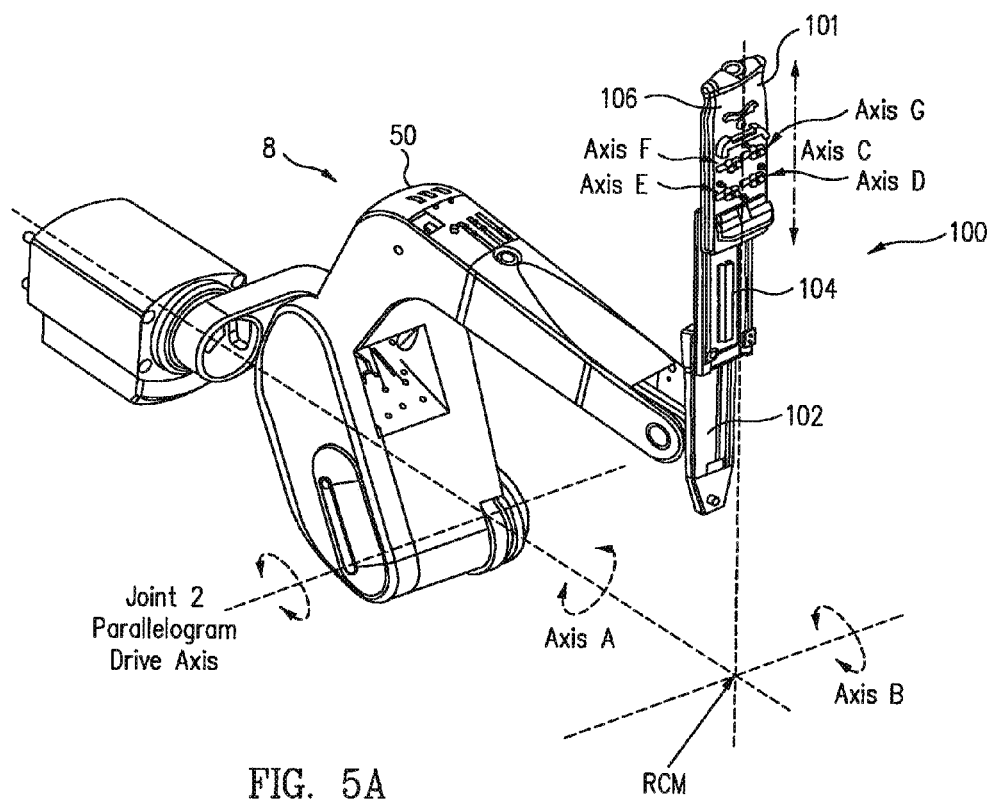

Referring now to FIGS. 5A-5E1, manipulator 8 including a telescopic insertion axis 100 is shown in more detail in accordance with embodiments of the present invention. The insertion axis of the present invention is comprised of a three-stage telescopic linear axis including three links, in one example, movably coupled to one another via bearings, rails, pulleys, and cables, with the links narrowing in width or form factor moving from the proximal link toward the distal link. Advantageously, the present invention provides for one-handed port and one-handed instrument clutching, a larger range of motion, a narrower insertion arm, and greater insertion axis stiffness and strength with reduced inertia as a function of insertion depth, thereby helping to enable a two-quadrant surgery with a single setup (e.g., a colorectal surgery), and providing for more space and visibility near the surgical field.

FIGS. 5A-5E and 5B1-5E1 illustrate perspective views and respective side views of manipulator 8 including a manipulator arm 50, and telescopic insertion axis 100 operably coupled to a distal end of arm 50 in accordance with an embodiment of the present invention. Telescopic insertion axis 100 includes a first link or base link 102, a second link or idler link 104 operably coupled to base link 102, and a third link or carriage link 106 operably coupled to idler link 104.

Base link 102 is operably coupled to a distal end of manipulator arm 50, and in one example has an accessory clamp 108 attached to a distal end of base link 102. An accessory 110, such as a cannula, may be mounted onto accessory clamp 108. An example of applicable accessory clamps and accessories are disclosed in pending U.S. application Ser. No. 11/240,087, filed Sep. 30, 2005, the full disclosure of which is incorporated by reference herein for all purposes. An example of applicable sterile adaptors and instrument housings are disclosed in U.S. application Ser. No. 11/314,040, filed Dec. 20, 2005, now U.S. Pat. No. 7,666,191, and in U.S. application Ser. No. 11/395,418, filed Mar. 31, 2006, now U.S. Pat. No. 7,699,855, the full disclosures of which are incorporated by reference herein for all purposes.

Carriage link 106 includes an instrument interface 101 for operably coupling to an instrument sterile adaptor (ISA) 109, which is capable of operably coupling to a housing of an instrument (e.g., housing 24 of FIGS. 3 and 5), and controls the depth of the instrument inside a patient. In one embodiment, the sterile adaptor is integrated with a drape that may be draped over the robotic surgical system, and in particular the manipulator system, to establish a sterile barrier between the non-sterile PSM arms and the sterile field of the surgical procedure. An example of an applicable drape and adaptor is disclosed in pending U.S. application Ser. No. 11/240,113, filed Sep. 30, 2005, the full disclosure of which is incorporated by reference herein for all purposes.

Idler link 104 is movably coupled between base link 102 and carriage link 106 to allow the links 102, 104, and 106 to move relative to one another along a lengthwise axis (e.g., axis C) in a telescoping fashion. In one embodiment, link 102 has a narrower form factor than link 104, and link 104 has a narrower form factor than link 106, thus providing for greater visibility near the surgical field.

Motion along axes C through G in manipulator 8, as shown in FIGS. 5A and 5A1, are provided by cables extending at least between the proximal and distal links in accordance with the present invention. The robotic arm can then control a tool or instrument operably coupled to the arm. The cables are a component of a transmission system also including drive pulleys, capstans, idler pulleys, and/or output pulleys, which are driven by electric motors. A pulley bank is located on an underside of base link 102 for passing cables and electrical wires between insertion axis 100 and manipulator arm 50 of manipulator system 6. A plurality of motion feed-throughs, in addition to other elements, may also be provided for transferring motion.

The drive assembly may further include a plurality of drive motors coupled to the arm for rotation therewith. Yaw and pitch motors control the motion of the arm about the A axis and the B axis (FIG. 5A), respectively, and drive motors control the motion of the wrist unit and insertion position. In one embodiment, four drive motors are mounted proximally in the arm to control four degrees of freedom of the tool mounted distally on the arm (the D, E, F, and G axes). Also, a proximally mounted motor controls the insertion position of the tool distally on the arm (along the C axis). The drive motors will preferably be coupled to encoders and potentiometers (not shown) to enable the servomechanism. Embodiments of the drive assembly, arm, and other applicable parts are described for example in U.S. Pat. Nos. 6,331,181, 6,491,701, and 6,770,081, the full disclosures of which (including disclosures incorporated by reference therein) are incorporated herein by reference for all purposes. The manipulator arm and the drive assembly may also be used with a broad range of positioning devices. A more complete description of a remote center positioning device can be found in U.S. patent application Ser. No. 08/504,301, filed Jul. 20, 1995, now U.S. Pat. No. 5,931,832, the complete disclosure of which is incorporated herein by reference for all purposes.

Referring now to FIGS. 6A-6E, a perspective view of an instrument interface 101 of a carriage link 106 for receiving an instrument sterile adaptor and ultimately an instrument (e.g., instrument 5) is illustrated in accordance with an embodiment of the present invention. Instrument interface 101 includes a shroud 502 to isolate electrical contacts 510 (e.g., from accidental contact), a spring-loaded input 504 for providing preload to ISA discs, each input having bosses 505 for delivering torque to the surgical instrument, a spring plunger 506 for providing preload to the ISA's retractor plate, a bracket 508 to hold ISA 109 in place, a lever 511 for securing/releasing the ISA, and a fiducial 512 also used to fix the position of the sterile adaptor relative to the robotic manipulator. In one example, instrument interface 101 includes four spring loaded inputs 504 with each input having two bosses 505, four spring plungers 506, and seven electrical contacts 510.

Figures 7A, 7B:
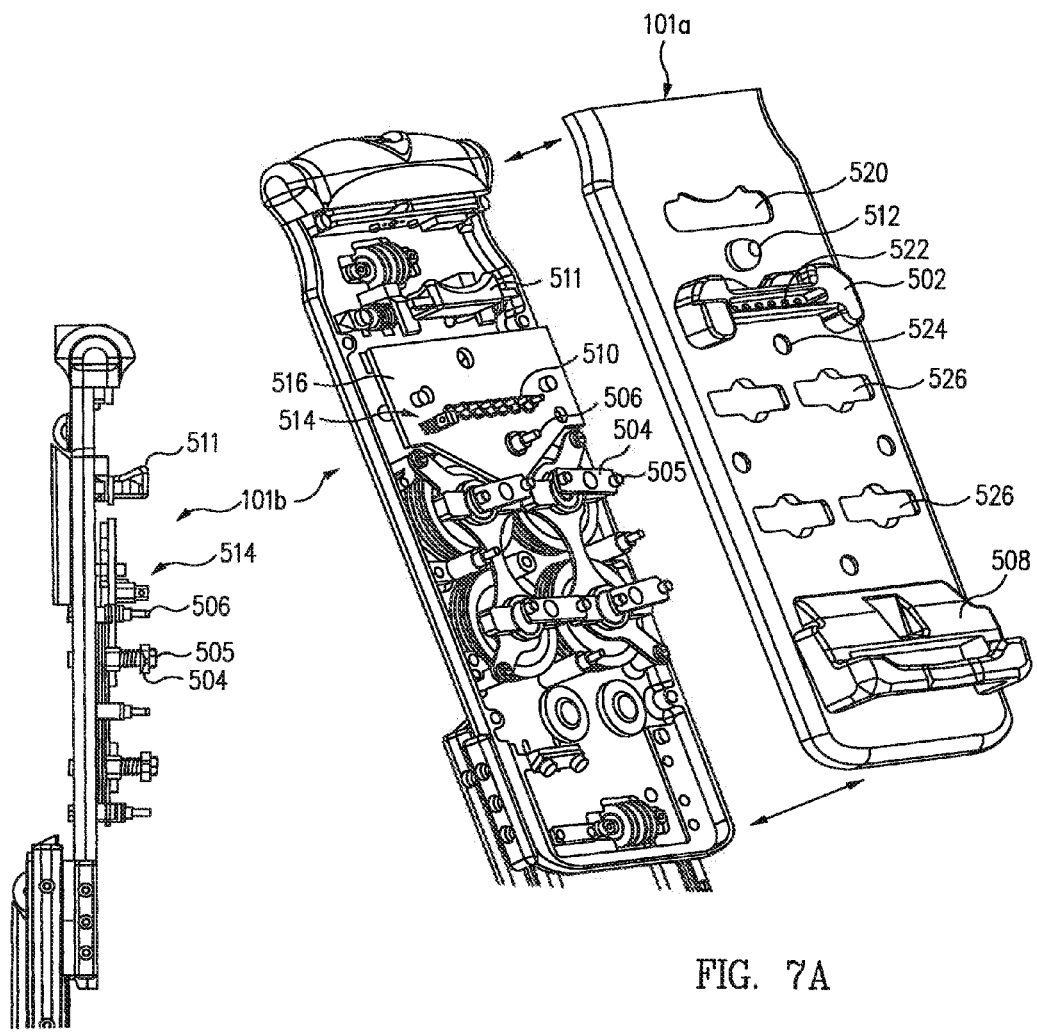
FIGS. 7A-7D illustrate different views of the interior of the carriage link in accordance with an embodiment of the present invention.

Referring now to FIGS. 7A-7D, the carriage link is illustrated with an instrument interface cover 101a separated from a remaining portion of the carriage link in accordance with an embodiment of the present invention. The present invention provides a compact apparatus and method to efficiently package the instrument interface components on the output end of a surgical robot. These components include but are not limited to circuit boards, cable transmission elements, sensors, and levers. FIG. 7A illustrates instrument interface cover 101a and the interior instrument interface components 101b of carriage link 106. Cover 101a includes fiducial 512, shroud 502 including openings 522 for electrical contacts 510, mounting bracket 508, an opening 520 for the lever 511, openings 524 for spring plungers 506, and openings 526 for spring loaded inputs 504. This "clamshell" or cover design for the instrument interface allows for easy access to the internal mechanisms, circuit boards, and cable transmission elements of the insertion axis when necessary.

Figure 7C:
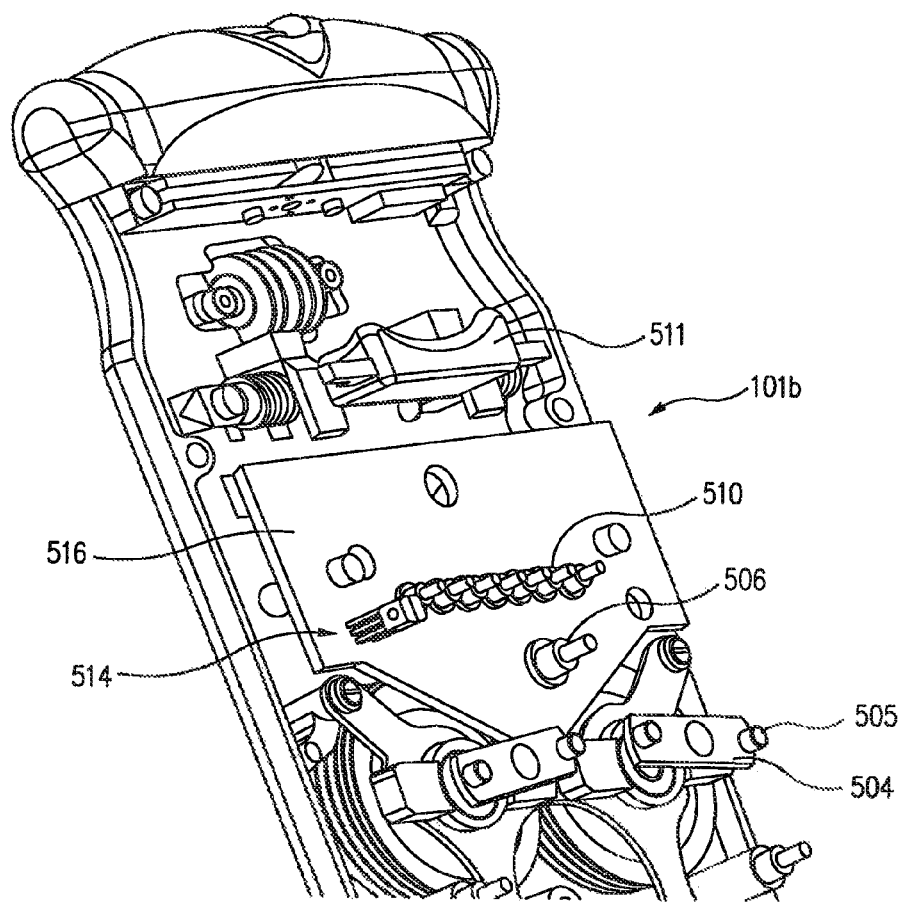

FIGS. 7A-7C also illustrate electrical contacts 510 and a Hall-effect sensor 514 operably mounted to a printed circuit assembly (PCA) 516, Electrical contacts 510 provide the interface to pass electrical signals between the ISA 109 and the PCA, and in one example may include "pogo pins". In one embodiment, the remote PCA 516 may have inputs and outputs for providing power and/or communicating with LEDs, Hall effect sensors, a sterile adaptor, an instrument, and a user interface button (e.g., for a clutch operation). The remote PCA 516 may also include an input for receiving power and an input/output for communicating with a main PCA (e.g., processor 4 of FIG. 1). In one embodiment, the main PCA may have inputs and outputs for providing power and/or communicating with motors (e.g., the main PCA transmits position controls to the motors and processes potentiometer and encoder signals), sensors, the user interface button, the remote PCA, and other printed circuit boards on a patient side cart system via a serial communication bus. An example of the inputs and outputs of applicable PCAs are described in U.S. application Ser. No. 11/613,915, filed Dec. 20, 2006, entitled "Wireless Communication In A Robotic Surgical System", the complete disclosure of which has been previously incorporated herein by reference for all purposes. The remote PCA may include, in one example, an Embedded Serializer for Instrument Interface (ESII) PCA, and the main PCA may include, in one example, an Embedded Serializer Patient Manipulator (ESPM) PCA, both available from Intuitive Surgical, Inc. of Sunnyvale, Calif.

Hall-effect sensor 514 is used to provide a robust means and method to detect the presence of an instrument mounted on ISA 109. Hall-effect sensors are desirable because they are solid-state devices with no moving parts. FIGS. 7A and 7C illustrate Hall-effect sensors 514 without a protective cover, and FIG. 7B illustrates a side view of the Hall-effect sensors 514 with a protective cover. In one embodiment, two adjacent Hall-effect sensors may be used to change state in the presence of a magnet in the instrument chassis. When the instrument magnet comes within close proximity to the Hall-effect sensors, the electrical output state of the sensors changes. PCA 516 detects the change in state of the sensors and notifies the system that an instrument is mounted. PCA 516 may also be able to detect the presence of other system components, such as an ISA or an instrument, via presence detection circuitry.

Figure 7D:
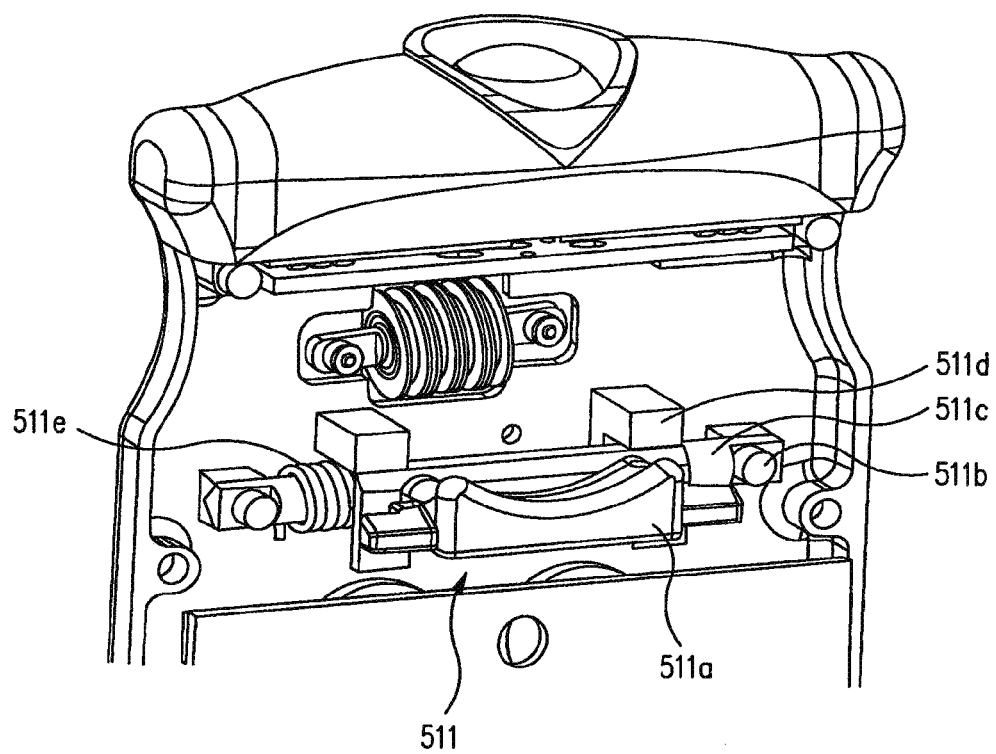
Figure 8A:
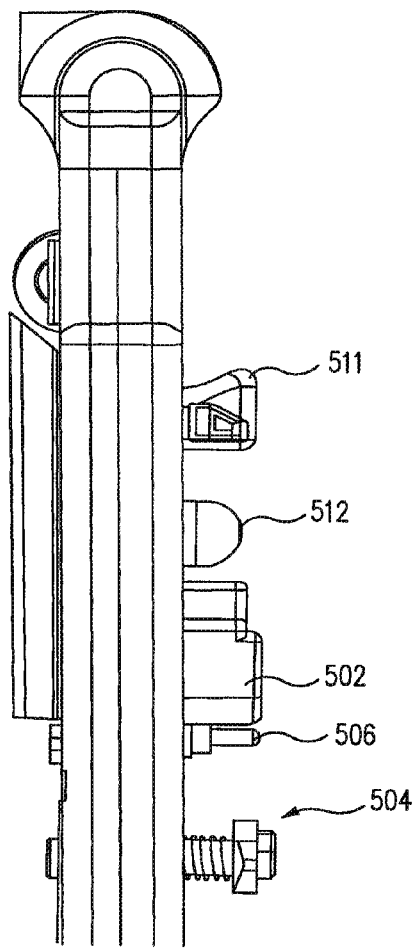
FIGS. 8A-8B illustrate the movement of a sterile adaptor engagement lever in accordance with an embodiment of the present invention.
Figure 8B:
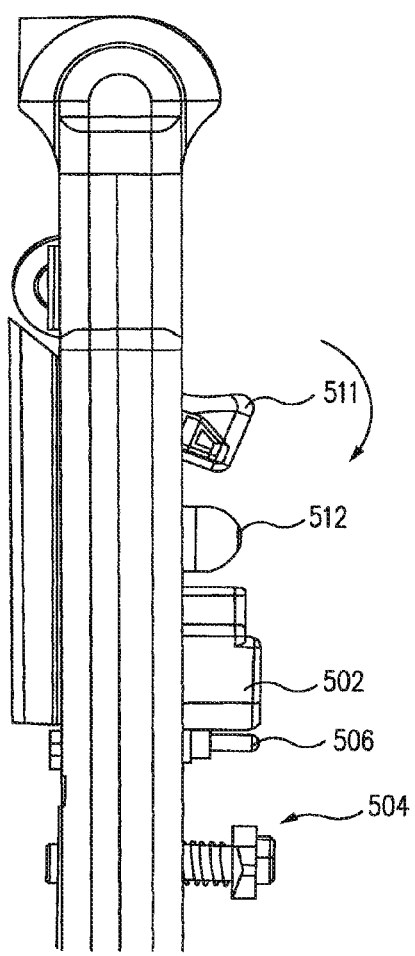

In another example, in addition to the Hall-effect sensors, a third input may be required for the system to recognize an instrument is mounted. The output of Hall-effect sensors 514 may be used in conjunction with an electrical circuit (e.g., a loopback circuit) that closes in the presence of the instrument thereby providing redundant presence confirmation. PCA 516 detects the closing of this circuit as well. FIG. 7D illustrates lever 511 for securing/releasing the ISA. Lever 511 includes a lever body 511a and mountings screws 511b for mounting a shaft 511c about which lever body 511a may rotate. A torsion spring 511e and hard stop 511d operate to place lever body 511a in a rest "up" position when the ISA is mounted and in a rotated position when the ISA is being installed or removed. Lever body 511a may rotate downward by approximately 25 degrees from a horizontal line. FIGS. 8A and 8B illustrate lever 511 in the rest position and in a rotated position, respectively.

Figure 9A:
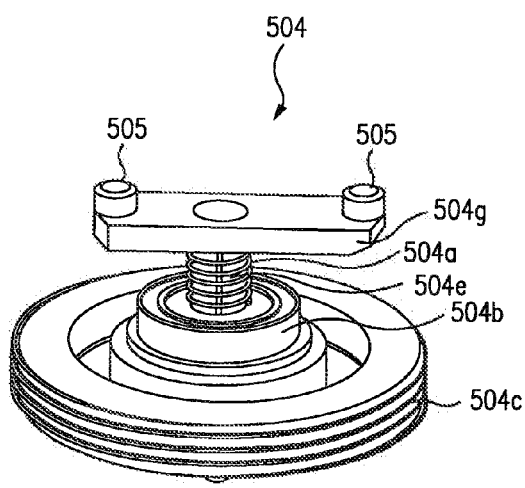
FIGS. 9A-9E are different views of an instrument input in isolation in accordance with an embodiment of the present invention.
Figure 9B:
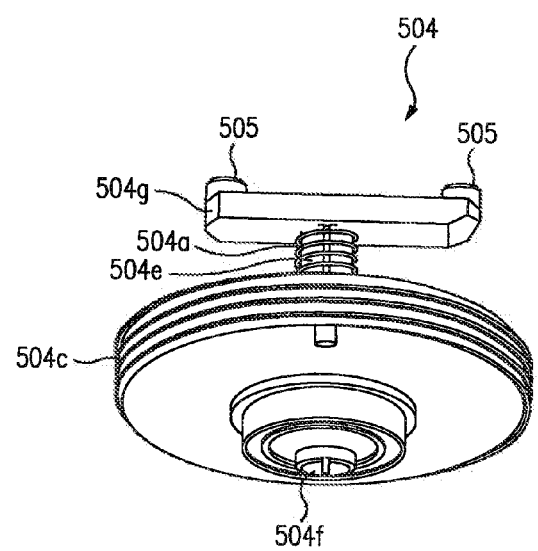
Figure 9C:
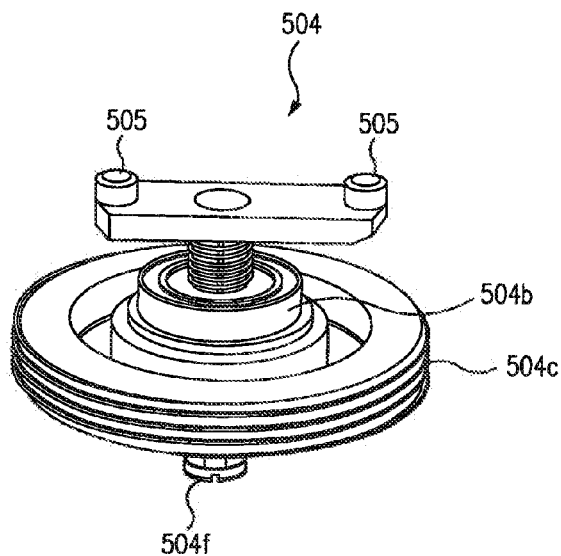
Figure 9D:
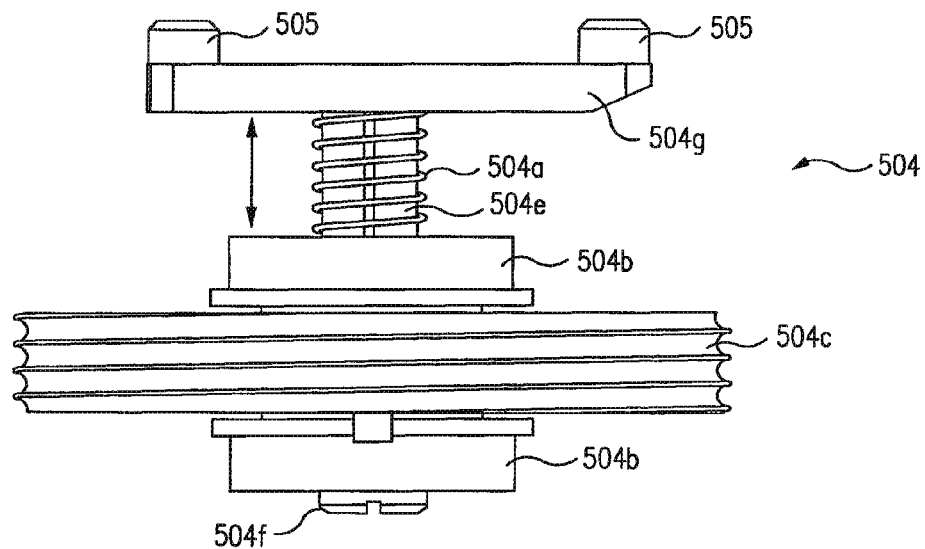
Figure 9E:
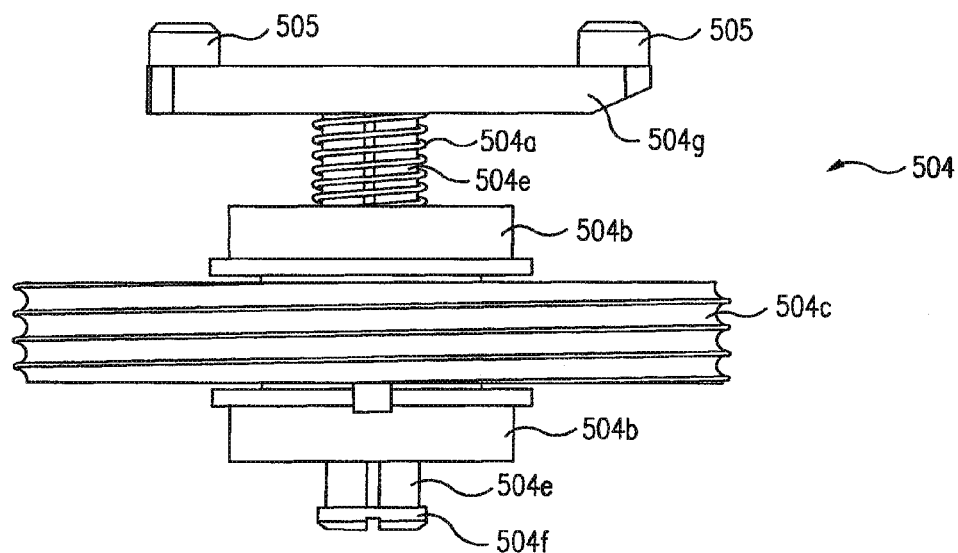
Figure 10A:
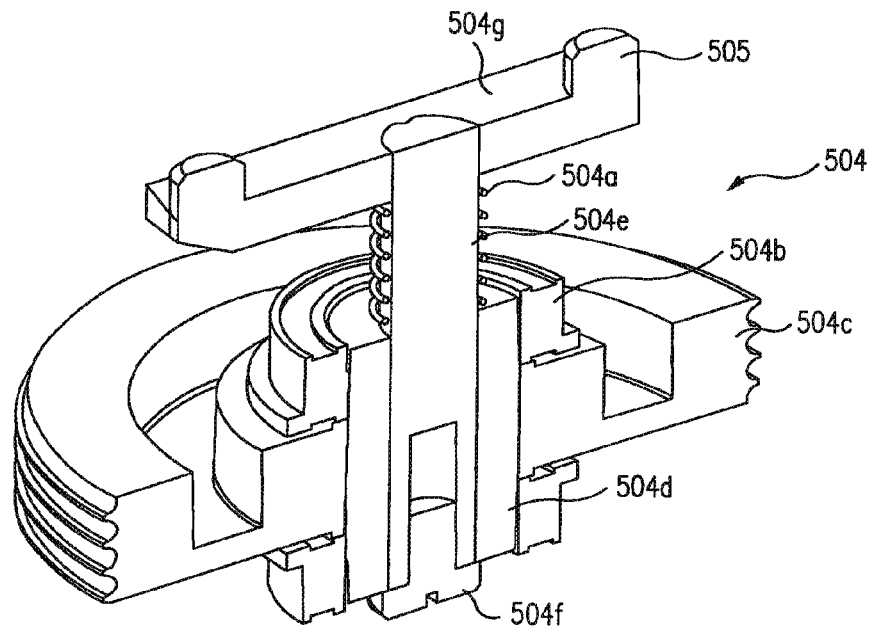
FIGS. 10A-10B are cross-sectional views of the instrument input in accordance with an embodiment of the present invention.
Figure 10B:
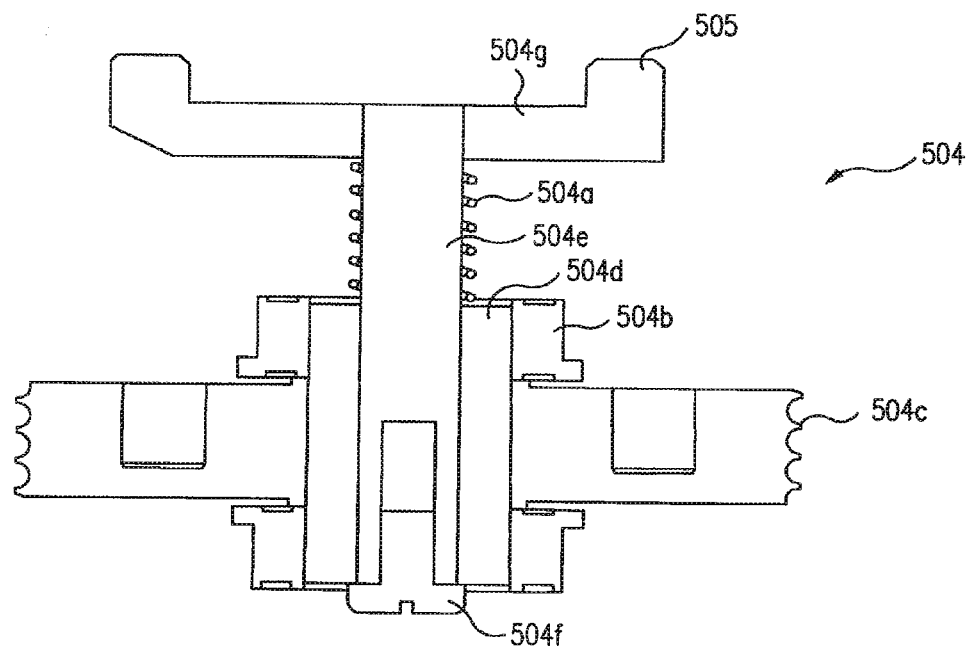

FIGS. 9A-9E are different views of an instrument input 504 in isolation, and FIGS. 10A-10B are cross-sectional views of the instrument input in accordance with an embodiment of the present invention. FIGS. 9A, 9B, and 9D illustrate input 504 in a rest (extended) position and FIGS. 9C and 9E illustrate input 504 in a retracted position. Input 504 includes a spring 504a, radial ball bearings 504b, an output pulley 504c, a linear ball spline slide unit 504d, a ball spline shaft 504e, a screw 504f, and an input bar 504g including bosses 505. Other means may also be used to achieve linear motion and torque transfer, such as linear slides, v-rollers, sliding bushings, ball screws, etc.

Figure 12A:
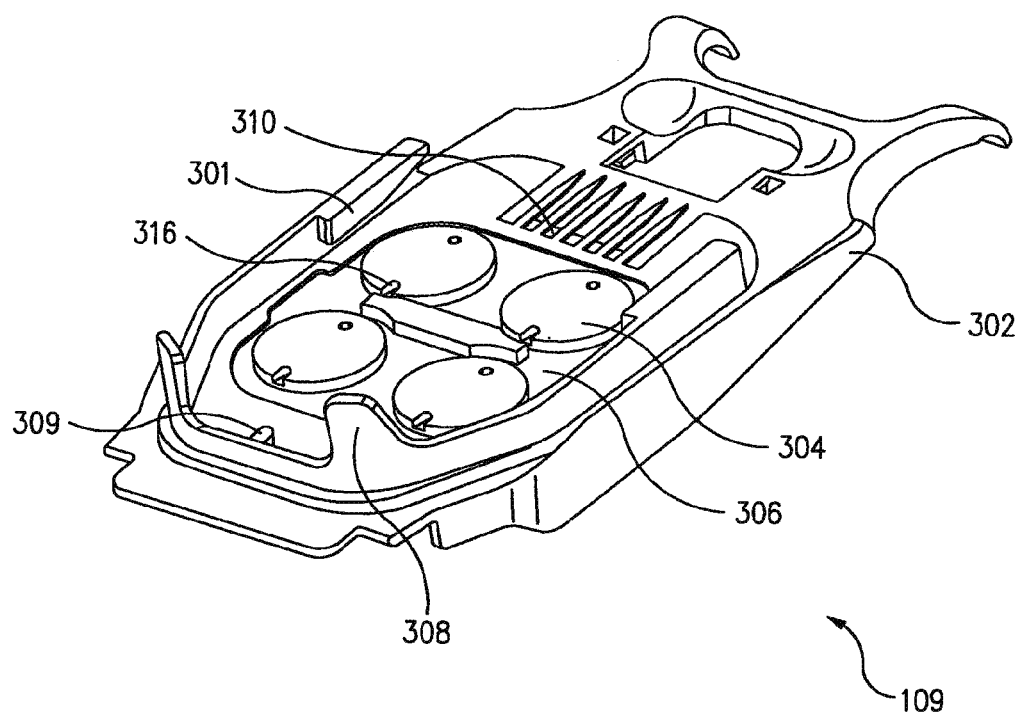
FIGS. 12A-12C illustrate a top perspective view, a bottom perspective view, and a sectional view, respectively, of a sterile adaptor, in accordance with an embodiment of the present invention.

Spring 504a provides a spring force in the axial direction of shaft 504e (an axial load) (shown by the double sided arrow in FIG. 9D), thereby allowing the input bar 504g to linearly translate in the axial direction. Radial ball bearings 504b enable the rotational motion of the assembly about the longitudinal (or lengthwise) axis of shaft 504e, and ball spline slide unit 504d supports the rotational motion of the assembly, in particular the rotational motion of shaft 504e and therefore input bar 504g, which allows for the transfer of torque from output pulley 504c to the instrument via ISA discs 304 (FIG. 12A). In one example, ball spline slide unit 504d is clamped to the output pulley and includes two tracks of recirculating balls which serve as the rolling elements in the direction of motion of the spline shaft 504e. Output pulley 504c is driven by cables, as disclosed in U.S. application Ser. No. 11/613,578, filed Dec. 20, 2006, entitled "Cable Tensioning In A Robotic Surgical System", the full disclosure of which (including all references incorporated by reference therein) has been previously incorporated by reference herein for all purposes. In one example, spline shaft 504e includes two grooves along its length that the recirculating balls ride in. Screw 504f is threaded into spline shaft 504e to provide a hard stop in the axial direction. Input bar 504g is pressed onto spline shaft 504e, in one example, and provides bosses 505 that engage into holes in the sterile adaptor discs.

Figure 11A:
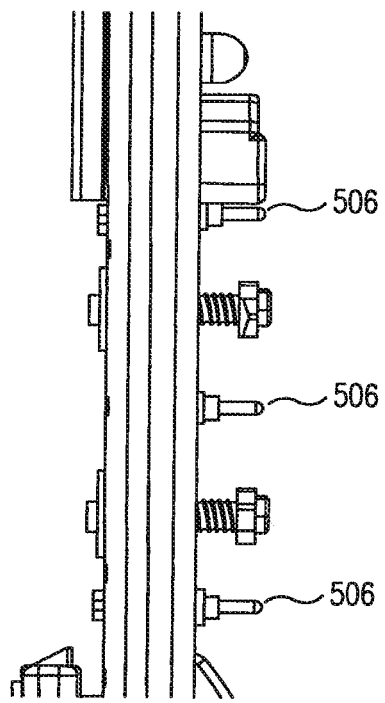
FIGS. 11A-11B are side views of the spring plungers in accordance with an embodiment of the present invention.
Figure 11B:
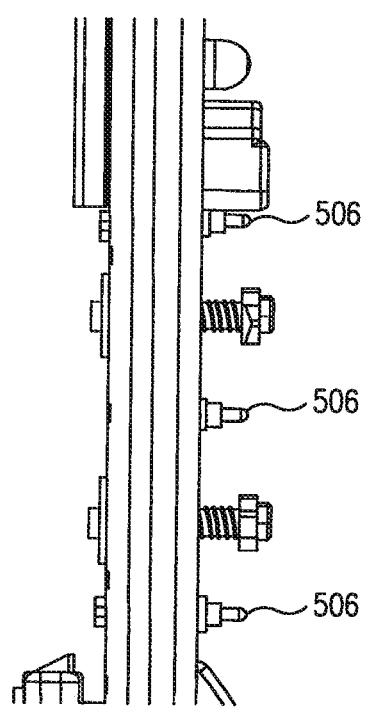

FIGS. 11A-11B are side views of the spring plungers in accordance with an embodiment of the present invention. FIG. 11B illustrates spring plungers 506 in a rest (extended) position and FIG. 11C illustrates spring plungers 506 in a retracted position when providing a bias against a retractor plate of ISA 109.

The spring-loaded inputs 504, spring plungers 506, and lever 511 provide spring elements on the manipulator, thereby allowing for a disposable design for the ISA and sterile barrier. Advantageously, the manipulator and ISA installment and engagement is easier to use, more reliable and requires less effort while enabling a cost-effective and disposable design for the ISA and a sterile barrier drape.

Figure 12B:
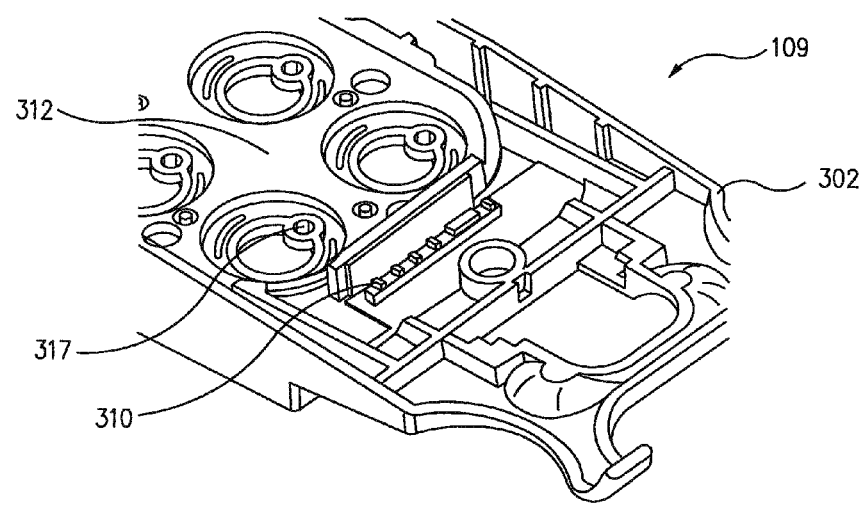
Figure 12C:
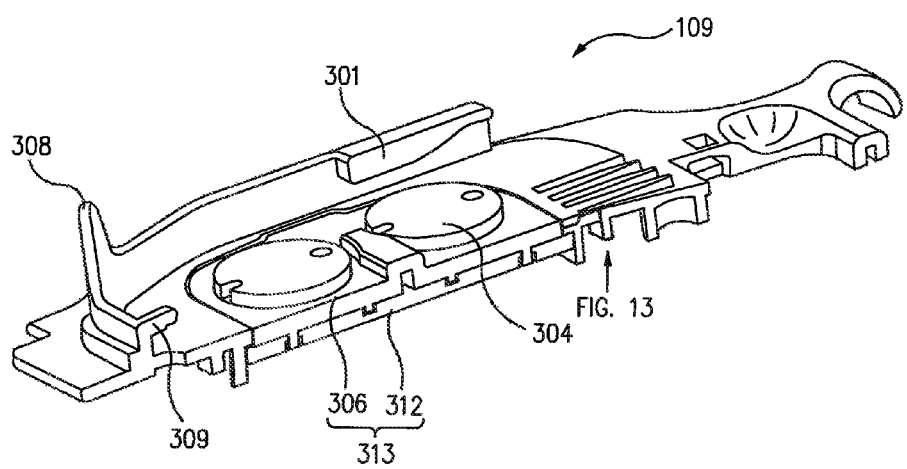

Referring now to FIGS. 12A, 12B, and 12C, a top perspective view, a bottom perspective view, and a sectional view of ISA 109, respectively, are illustrated in accordance with an embodiment of the present invention. ISA 109 includes a housing 302, a disc 304, a top retractor plate 306, an instrument stop feature 308 of housing 302, a rail feature 301 of housing 302, a contact 310, and a bottom retractor plate 312. Top retractor plate 306 and bottom retractor plate 312 form a retractor plate assembly 313 which moves relative to housing 302. Discs 304 are captured inside of retractor plate assembly 313 and move relative to the retractor plate assembly.

Figure 13:
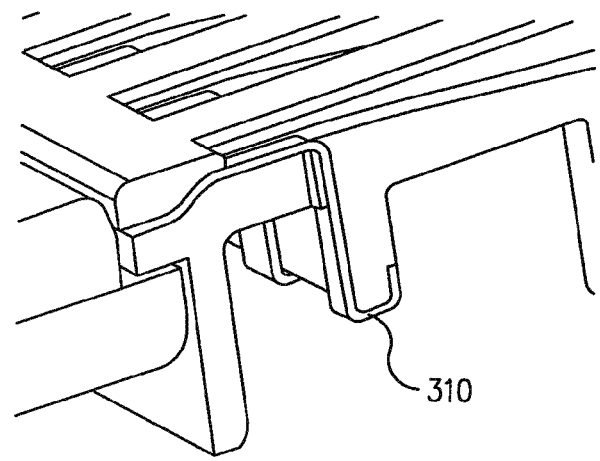
FIG. 13 illustrates a close up section view of an electrical contact of the sterile adaptor in accordance with an embodiment of the present invention.

FIG. 13 illustrates a close up sectional view of a contact 310, which is insert molded into the housing in one embodiment.

Figure 14A:
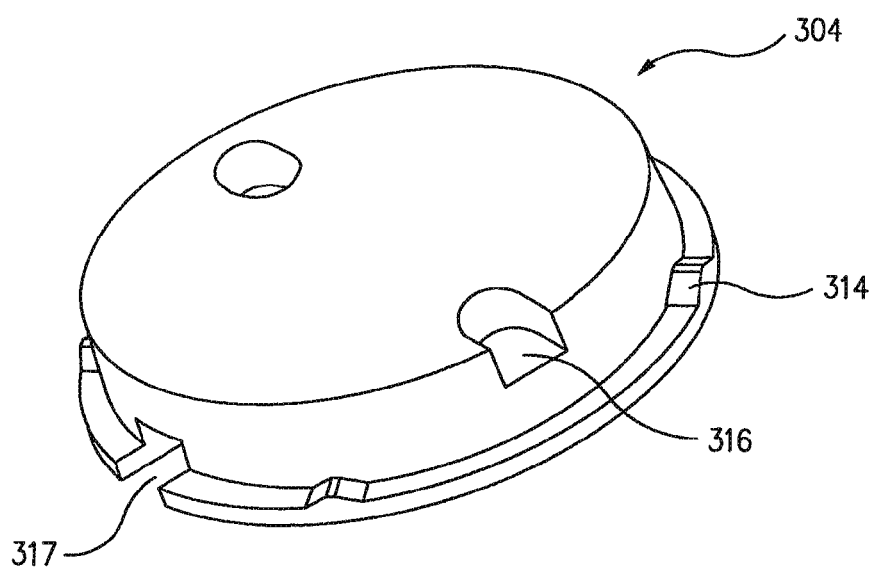
FIGS. 14A and 14B illustrate close up perspective top and bottom views of a disc of the sterile adaptor, respectively, in accordance with an embodiment of the present invention.
Figure 14B:
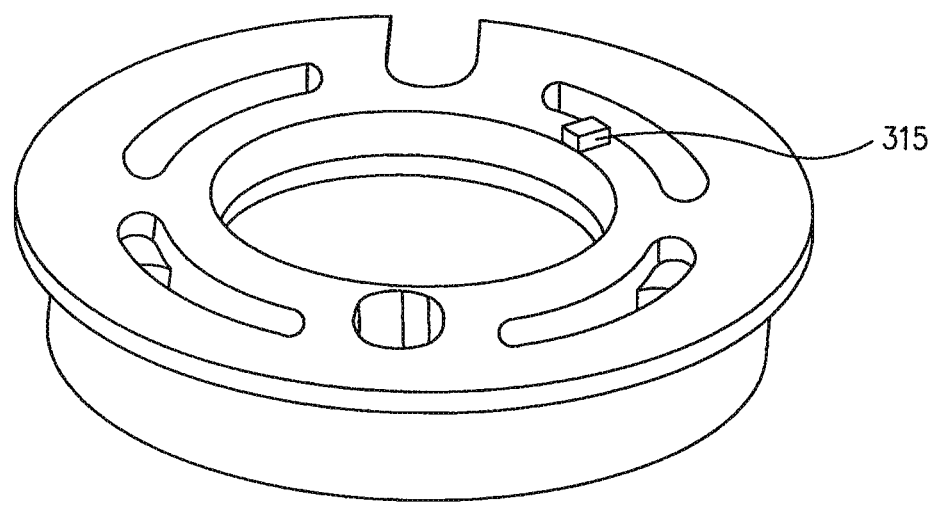

FIGS. 14A and 14B illustrate close up perspective top and bottom views of disc 304, respectively, which includes a tooth 314 at the base of disc 304, a hole 316 in the body of disc 304 for accepting pins 253 of a surgical instrument 5 (see FIGS. 16D and 16E), a hole 317 in the bottom of disc 304 for receiving bosses 505 of spring loaded inputs 504 (see FIGS. 9 and 10), and a tab 315 for moving disc 304 out of a dead zone, in accordance with an embodiment of the present invention. In this embodiment ISA 109 includes four discs 304 with each disc 304 including four teeth 314 and two holes 316. The four teeth 314 are placed 90 degrees apart in one embodiment. It is noted that in other embodiments, more or less discs, teeth, and slots are possible but need to operably couple to an adaptor receiving portion on the manipulator and a surgical instrument.

Figures 15A, 15B:
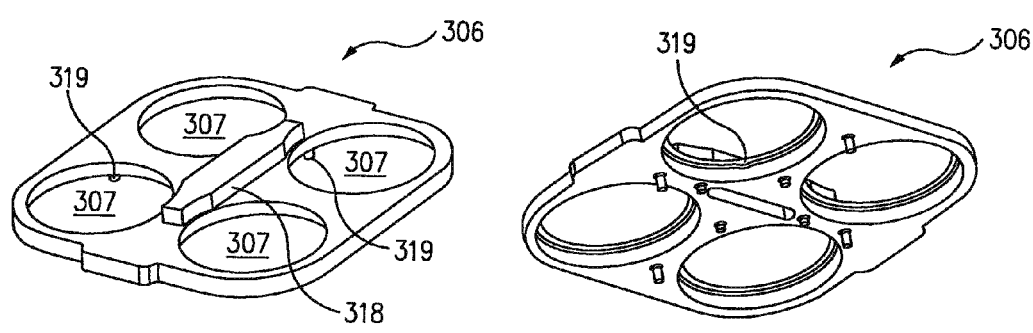
FIGS. 15A and 15B illustrate top and bottom perspective views of a top retractor plate of the sterile adaptor in accordance with an embodiment of the present invention.

FIGS. 15A and 15B illustrate top and bottom perspective views of top retractor plate 306 in accordance with an embodiment of the present invention. Top retractor plate 306 includes a bar 318 for engaging the instrument chassis 24 and a tooth 319 for mating with a tooth 314 of disc 304 depending on relative position. As shown, top retractor plate 306 includes four apertures 307 for the four discs 304.

Referring now to FIGS. 16A through 16F, installation/engagement of an instrument sterile adaptor (ISA) 109 to instrument interface 101 (FIG. 16A), installation/engagement of surgical instrument 5 to ISA 109 (FIGS. 16B-16E), and removal of surgical instrument 5 from ISA 109 (FIG. 16F) are illustrated in accordance with an embodiment of the present invention.

Figure 16A:
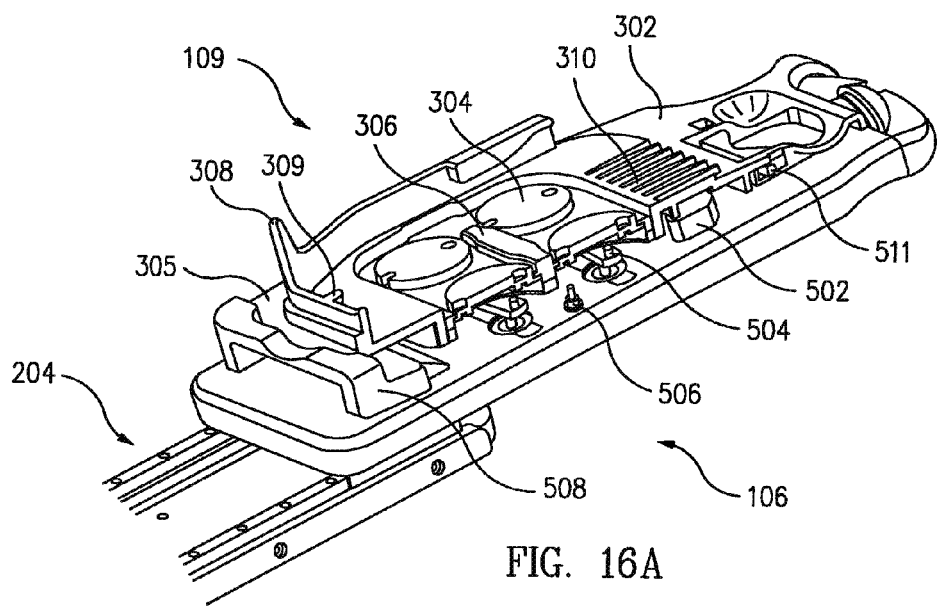
FIGS. 16A-16F show installation/engagement of the sterile adaptor to the instrument interface, installation/engagement of the surgical instrument to the sterile adaptor, and removal of the surgical instrument from the sterile adaptor in accordance with an embodiment of the present invention.

FIG. 16A shows ISA 109 installed and engaged with adaptor receiving portion 101 of manipulator 8. ISA contacts 310 are coupled to manipulator contacts 510, discs 304 are engaged with spring loaded inputs 504, bottom retractor plate 312 is engaged with spring plungers 506, and tongue feature 305 (FIGS. 16A and 16F) mates with bracket 508. Instrument stop feature 308 allows for stopping of the instrument (for patient safety) if the user misses the rails 301 when installing the instrument onto the ISA. The instrument is fully stopped by bar 318 on top retractor plate 306 when installed. Prior to installation, spring loaded inputs 504 and spring plungers 506 are at their most extended position, and discs 304 of the ISA are free to rotate to any random location within the retractor plate assembly. In one embodiment, to install ISA 109 onto the adaptor-receiving portion of interface 101, the user places the tongue of the ISA housing into a bracket and swings the back end down thereby engaging a lever/latch 511.

In this installed but pre-engaged position, discs 304 are pressed upward against top retractor plate 306 by spring loaded inputs 504, and retractor plate assembly 313 is pressed upward by spring loaded inputs 504 and spring plungers 506. In each disc location (aperture 307 of retractor plate 306), there is one tooth 319 on the retractor plate 306 which engages with teeth 314 of disc 304. The teeth configuration has multiple functions, one of which is to push discs 304 out of a "dead zone" which is an angular orientation where the holes 317 in the bottom of disc 304 are in a position where they may not mate with bosses 505 of spring loaded inputs 504 since they do not rotate through a full 360 degrees. Another function of the teeth configuration is to prevent disc 304 from rotating more than 90 degrees during the sterile adaptor engagement sequence.

During the engagement sequence, disc teeth 314 mesh with retractor plate teeth 319 as spring loaded inputs 504 are activated to impart movement of disc 304 through friction between bosses 505 and the bottom surface of disc 304 and through contact with tab 315. When the spring loaded inputs 504 reverse rotational direction, the presence of the four teeth 314 stops this rotational motion of disc 304, and bosses 505 are allowed to line up with holes 317 of disc 304 as the spring loaded inputs 504 rotate relative to disc 304. As holes 317 on the bottom of disc 304 and bosses 505 of spring loaded inputs 504 align, discs 304 drop onto spring loaded inputs 504. At this point, the teeth 319 of top retractor plate 306 clear the teeth 314 of disc 304 as disc 304 is dropped down, thereby allowing disc 304 to move freely relative to retractor plate 306. When discs 304 are engaged onto spring loaded inputs 504, ISA 109 is engaged with adaptor receiving portion 101.

In one embodiment, the engagement sequence happens in milliseconds after installation of ISA 109 onto adaptor receiving portion 101. As ISA 109 is swung down into position, electrical contacts 310 engage electrical contacts 510 (e.g., pogo pins) such that an initially open circuit on the manipulator 8 is closed, which activates the ISA engagement sequence. It is noted that the insert-molded contact 310 in housing 302 may have multiple electrical paths (vias) which engage with contacts on the adaptor receiving portion 101, and which are also used to establish communication with a surgical instrument 5 via instrument electrical contacts 255 (FIGS. 16C and 16D).

Figure 16B:
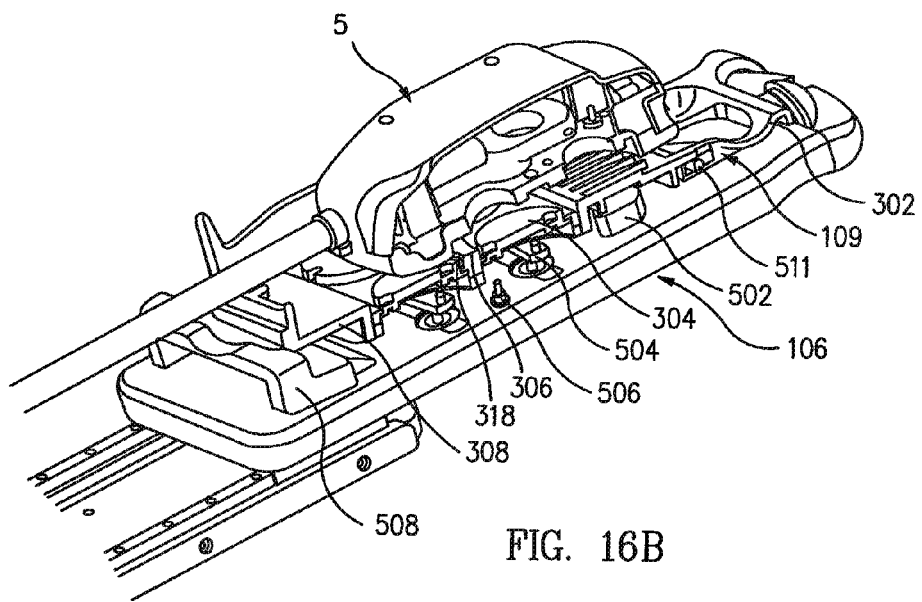
Figure 16C:
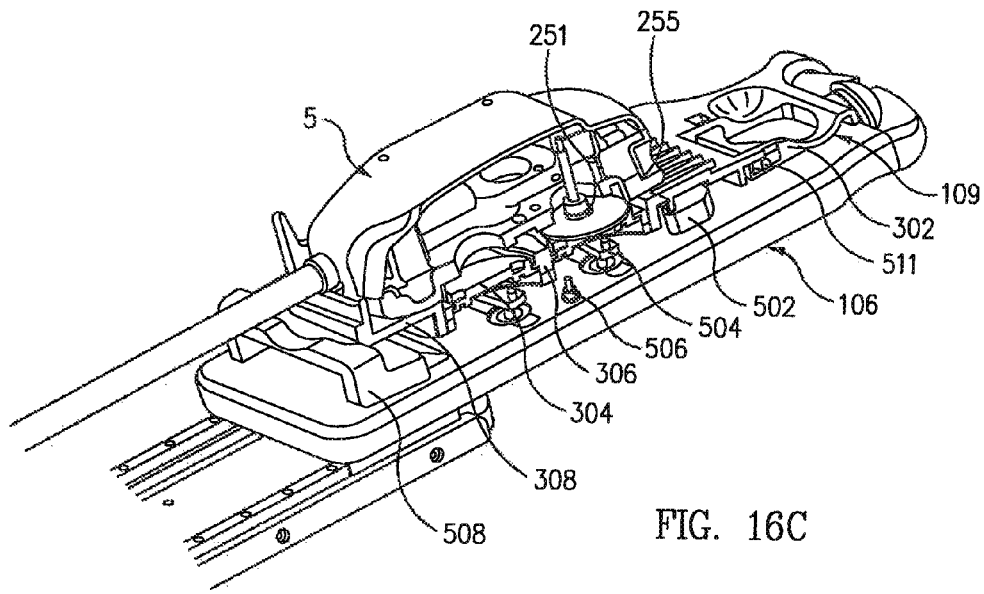

FIG. 16B shows surgical instrument 5 partially installed, and FIG. 16C shows surgical instrument 5 fully installed and engaged with ISA 109. Initially, as the user installs surgical instrument 5 onto ISA 109, retractor plate assembly 313 is pushed down toward adaptor receiving portion 101 as top retractor plate 306 is pressed down by instrument 5 engaging center bar 318. Prior to electrical engagement between instrument 5 and ISA 109, a chamfer on bar 318 engages a chamfer on the bottom of instrument 5, and as these two chamfers are aligned, the instrument is pulled into its home position due to the spring force of the spring loaded inputs and spring plungers. As the instrument is pulled into its home position, retractor plate assembly 313 begins to rise up into the surgical instrument, and in substantially the same motion, the electrical contacts 255 of instrument 5 come into contact with electrical contacts 310 of ISA 109. When instrument 5 is installed onto ISA 109, top retractor plate 306 is pressing on the bottom of the instrument and bar 318 is inside a clearance slot in the instrument housing. Prior to instrument engagement, discs 304 and spring loaded inputs 504 are pressed away from the instrument since the inputs on the instrument are not engaged with the holes 316 on the top of disc 304.

Figure 16D:
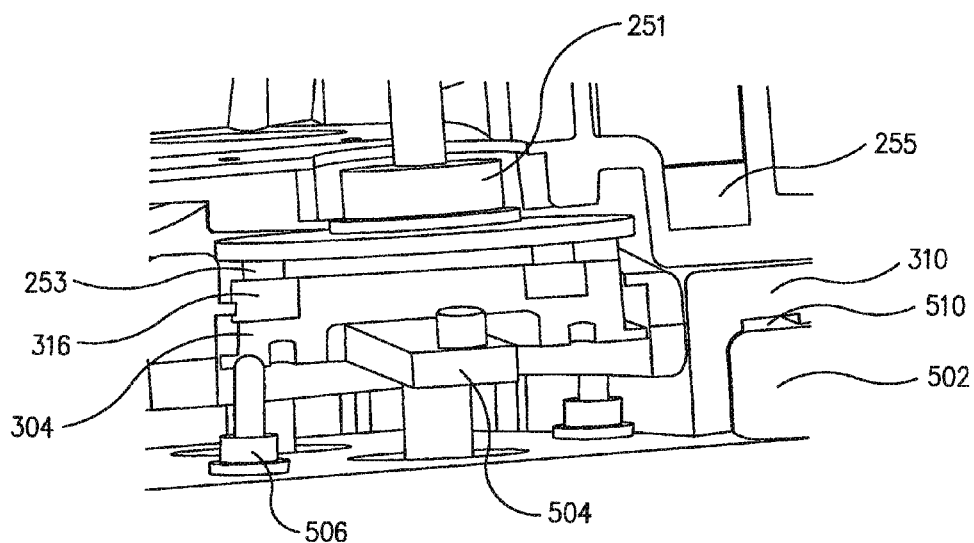
Figure 16E:
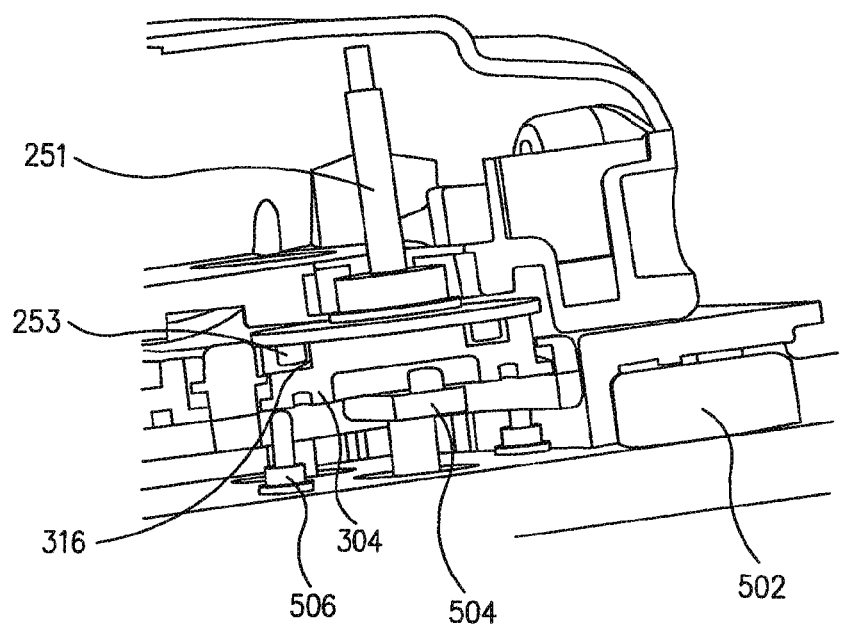

FIGS. 16D and 16E illustrate an engagement sequence of disc 304 with instrument 5. In FIG. 16D, disc 304 is not engaged with instrument 5 until disc 304 rotates to align with instrument disc 251, which is initially in a random position. As previously mentioned with respect to the engagement sequence between ISA 109 and adaptor receiving portion 101, as the electrical contacts of the instrument engage the contacts 310 of ISA 109, a normally open circuit between the ESII printed circuit board and instrument, through the ISA, is closed which activates the instrument engagement sequence. Spring loaded inputs 504 and discs 304 rotate together as an assembly until the holes 316 of disc 304 engage with the pins 253 of instrument disks 251. When the holes are aligned with the pins, disc 304 and spring loaded inputs 504 are allowed to move upwards. FIG. 16E shows instrument disk 251 having a pin 253 which engages with hole 316 of ISA disk 304. At this point instrument 5 is considered engaged with ISA 109. It is noted that other contacts on ISA 109 may transmit electrical signals between the surgical system and an instrument "Reposable Tool Interface" (RTI) board.

When the instrument is fully installed, it is held in position at three points along its housing. Two points are at the rail features 301 along the sides of the instrument, and a third point is at the center hold down tab 309 along the front center of the instrument. Advantageously, by holding down the instrument at three locations, the instrument is not over-constrained and installation and removal is made easier.

Figure 16F:
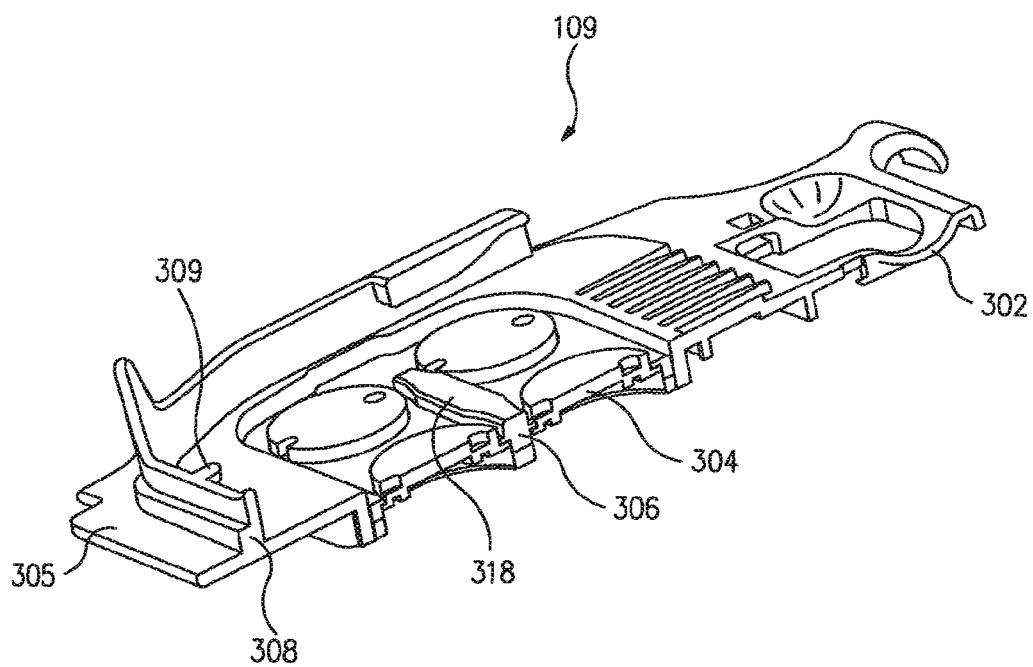

FIG. 16F illustrates removal of instrument 5 (not shown) from ISA 109. When the user wants to remove the instrument, levers on either side of the instrument chassis are squeezed and the instrument is pulled back out of the ISA. The levers on the instrument act on the center bar 318 of the top retractor plate, which in turn pushes the retractor plate down away from the instrument. As the retractor plate moves further away, the discs 304 are disengaged from the pins of the instrument allowing for removal of the instrument.

Embodiments described above illustrate but do not limit the invention. It should also be understood that numerous modifications and variations are possible in accordance with the principles of the present invention. For example, the system is not limited to four robotic manipulator assemblies, but may include two or more in other examples. Accordingly, the scope of the invention is defined only by the following claims.

We claim:

1. An instrument interface of a telesurgical manipulator, comprising:
   an instrument input including
      an elongated input bar having a length dimension greater than a width dimension, the elongated input bar adapted to transfer an axial load and torque to a sterile adaptor configured to operably couple an instrument;
      a spring member defining a load axis extending therethrough and adapted to provide the axial load to the elongated input bar along the load axis, wherein the load axis of the spring member is oriented orthogonally to the length dimension of the elongated input bar;
      an output pulley adapted to provide the torque to the input bar;
      a shaft, extending through the spring member, the shaft being rigidly coupled to the elongated input bar and movably coupled to the output pulley; and
      a slide unit coupled between the shaft and the output pulley, the slide unit adapted to transfer the torque from the output pulley to the shaft and adapted to translate axially along the shaft.

2. The instrument interface of claim 1, wherein the elongated input bar includes a projection extending along a projection axis for engaging the sterile adaptor to transfer the torque, wherein the projection axis intersects the elongated input bar between a distal end of the elongated input bar and the load axis.

3. The instrument interface of claim 1 wherein the shaft includes at least one spline engaged with the slide unit.

4. The instrument interface of claim 1 wherein the elongated input bar is coupled to an end of the shaft and a stop member is adjustably engaged with an opposite end of the shaft, wherein the stop member limits axial movement of the shaft relative to the output pulley.

5. The instrument interface of claim 1 wherein the instrument input is among a plurality of instrument inputs adapted to transfer axial load and torque to the sterile adaptor.

6. The instrument interface of claim 1 further comprising a spring-loaded plunger adapted to provide a preload to the sterile adaptor.

7. The instrument interface of claim 1 further comprising a plurality of electrical contacts that provide an electrical interface with the sterile adaptor.

8. A telerobotic surgical manipulator system, comprising:
   a manipulator assembly, including:
      a base link operably coupled to a distal end of a manipulator arm; and
      a carriage link movably coupled to the base link along a lengthwise axis, the carriage link including an instrument interface including:
         an instrument input including
            an input bar adapted to transfer an axial load and torque to a sterile adaptor configured to operably couple an instrument;
            a spring member adapted to provide the axial load to the input bar;
            an output pulley adapted to provide the torque to the input bar;
            a shaft that extends through the spring member, the shaft being coupled to the input bar and the output pulley; and
            a slide unit coupled between the shaft and the output pulley and adapted to transfer the torque from the output pulley to the shaft.

9. The system of claim 8, wherein the input bar includes a projection for engaging the sterile adaptor to transfer the torque.

10. The system of claim 8 wherein the the shaft is rigidly coupled to the input bar and movably coupled to the output pulley.

11. The system of claim 10 wherein the slide unit is adapted to translate axially along the shaft.

12. The system of claim 11 wherein the shaft includes at least one spline engaged with the slide unit.

13. The system of claim 10 wherein the input bar is coupled to an end of the shaft and a stop member is adjustably engaged with an opposite end of the shaft, wherein the stop member limits axial movement of the shaft relative to the output pulley.

14. The system of claim 8 further comprising a spring-loaded plunger adapted to provide a preload to the sterile adaptor.

15. The system of claim 8 further comprising a plurality of electrical contacts that provide an electrical interface with the sterile adaptor.

16. An instrument interface of a telesurgical manipulator, comprising:
    an instrument input including
        an elongated input bar having a length dimension greater than a width dimension, the elongated input bar adapted to transfer an axial load and torque to a sterile adaptor configured to operably couple an instrument;
        a spring member defining a load axis extending therethrough and adapted to provide the axial load to the elongated input bar along the load axis, the spring member positioned on a first side of the elongated input bar;
        a first projection and a second projection protruding from a surface of a second side of the elongated input bar, the first side and the second side being opposite sides of elongated input bar, and wherein the first projection and the second projection are offset from the load axis by different lengths to facilitate rotational alignment with a disc disposed in between the instrument input and an instrument; and
        an output pulley adapted to provide the torque to the input bar.

17. The instrument interface of claim 16, wherein the first projection has a first projection axis and the second projection has a second projection axis, wherein at least one of the first projection axis and the second projection axis is not coaxial with the load axis.

18. The instrument interface of claim 17, wherein the first and second projections align with a first opening and a second opening, respectively, in the disc at a single rotational position.

* * * * *